US009694036B2

(12) United States Patent
George et al.

(10) Patent No.: US 9,694,036 B2
(45) Date of Patent: Jul. 4, 2017

(54) PRODUCTION OF MIDBRAIN DOPAMINERGIC NEURONS AND METHODS FOR THE USE THEREOF

(71) Applicant: CELLULAR DYNAMICS INTERNATIONAL, INC., Madison, WI (US)

(72) Inventors: Matt George, Madison, WI (US); Carrie Chavez, Madison, WI (US); Chris McMahon, Madison, WI (US); Wen Bo Wang, Madison, WI (US); Lucas Chase, Madison, WI (US); Brad Swanson, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 0 days.

(21) Appl. No.: 14/664,245

(22) Filed: Mar. 20, 2015

(65) Prior Publication Data

US 2015/0265652 A1    Sep. 24, 2015

Related U.S. Application Data

(60) Provisional application No. 61/968,838, filed on Mar. 21, 2014.

(51) Int. Cl.
| | |
|---|---|
| *C12N 5/071* | (2010.01) |
| *C12N 5/079* | (2010.01) |
| *A61K 48/00* | (2006.01) |
| *A61K 35/30* | (2015.01) |
| *A61J 1/00* | (2006.01) |
| *B65D 25/20* | (2006.01) |
| *C12N 5/0793* | (2010.01) |
| *C12N 9/02* | (2006.01) |
| *C12Q 1/68* | (2006.01) |
| *G01N 33/50* | (2006.01) |

(52) U.S. Cl.
CPC .............. *A61K 35/30* (2013.01); *A61J 1/00* (2013.01); *B65D 25/205* (2013.01); *C12N 5/0619* (2013.01); *C12N 9/0071* (2013.01); *C12Q 1/6876* (2013.01); *G01N 33/5058* (2013.01); *C12N 2501/15* (2013.01); *C12N 2501/155* (2013.01); *C12N 2501/41* (2013.01); *C12N 2501/415* (2013.01); *C12N 2501/727* (2013.01); *C12N 2506/45* (2013.01); *C12Q 2600/136* (2013.01); *C12Q 2600/158* (2013.01); *C12Y 114/16002* (2013.01); *G01N 2333/4706* (2013.01)

(58) Field of Classification Search
None
See application file for complete search history.

(56) References Cited

U.S. PATENT DOCUMENTS

2003/0211605 A1    11/2003   Lee et al.
2013/0052268 A1*    2/2013   Chung ................ A61K 38/162
                                                       424/490

FOREIGN PATENT DOCUMENTS

| EP | 2 694 644 | 10/2012 |
| EP | 2 614 829 | 7/2013 |
| WO | WO 03/000868 | 1/2003 |
| WO | WO 2010/096496 | 8/2010 |
| WO | WO 2013/067362 | 5/2013 |

OTHER PUBLICATIONS

Jaeger et al., Development, 2011; 138 ;4369-4374.*
Suter et al., J Pathol 2008; 215:355-368.*
Studer, L., Progress in Brain Research, vol. 200, 2012, pp. 243-263.*
Nogueira et al., Oncogene, 2011; 30:3537-3548.*
Chambers et al., "Highly efficient neural conversion of human ES and iPS cells by dual inhibition of SMAD signaling," *Nature Biotechnology*, 27(3):275-280, 2009.
Cooper et al., "Differentiation of human ES and Parkinson's disease iPS cells into ventral midbrain dopaminergic neurons requires a high activity form of SHH, FGF8a and specific regionalization by retinoic acid," *Molecular and Cellular Neuroscience*, 45:258-266, 2010.
Doi et al., "Isolation of human induced pluripotent stem cell-derived dopaminergic progenitors by cell sorting for successful transplantation," *Stem Cell Reports*, 2:337-350, 2014.
Fasano et al., "Efficient derivation of functional floor plate tissue from human embryonic stem cells," *Cell Stem Cell*, 6(4):336-347, 2010.
Kriks et al., "Dopamine neurons derived from human ES cells efficiently engraft in animal models of Parkinson's disease," *Nature*, 480:547-553, 2011.
PCT International Search Report and Written Opinion issued in International Application No. PCT/US2015/021783, mailed May 26, 2015.
Perrier et al., "Derivation of midbrain dopamine neurons from human embryonic stem cells," *Proc. Natl. Acad. Sci. USA*, 101(34):12543-12538, 2004.
Sundberg et al., "Improved cell therapy protocols for Parkinson's disease based on differentiation efficiency and safety of hESC-, hiPSC-, and non-human primate iPSC-derived dopaminergic neurons," *Stem Cells*, 31:1548-1562, 2013.

* cited by examiner

*Primary Examiner* — Doug Schultz
(74) *Attorney, Agent, or Firm* — Parker Highlander PLLC

(57) ABSTRACT

Methods are provided for efficient production of midbrain dopaminergic (DA) neurons. In some aspects, methods involve differentiation and selection of DA neurons for a transgenic pluripotent cell population (e.g., cells comprising a selectable marker gene). Cell populations produced by the instant methods and methods of their use are likewise provided.

8 Claims, 8 Drawing Sheets

PRODUCTION OF MIDBRAIN DOPAMINERGIC NEURONS AND METHODS FOR THE USE THEREOF

The present application claims the priority benefit of U.S. provisional application No. 61/968,838, filed Mar. 21, 2014, the entire contents of which is incorporated herein by reference.

BACKGROUND OF THE INVENTION

1. Field of the Invention

The present invention relates generally to the field of molecular and cellular biology. More particularly, it concerns methods for producing midbrain dopaminergic neuronal cells from stem cells, such as induced pluripotent stem (iPS) cells.

2. Description of Related Art

Cell populations that retain the ability to differentiate into numerous specialized cell types are useful for developing large numbers of lineage specific differentiated cell populations. These lineage specific differentiated cell populations are contemplated to find use in cell replacement therapies for patients with diseases resulting in loss of function of a defined cell population. In addition to their direct therapeutic value, lineage specific differentiated cells are also valuable research tools for a variety of purposes including in vitro screening assays to identify, confirm, and test for specification of function or for testing delivery of therapeutic molecules to treat cell lineage specific disease.

In the case of Parkinson's disease, for example, it is the loss of midbrain dopaminergic (DA) neurons that results in the appearance of disease symptoms. Thus, there is need for methods of producing DA neuronal cells from pluripotent cells, since such cells could be used both therapeutically and in disease models, e.g., to identify new therapeutics for treatments for Parkinson's disease. However, conventional methods for differentiating DA neurons (see, e.g., Perrier et al., 2004) resulted in cell populations that exhibited poor in vivo engraftment and displayed markers that were inconsistent with authentic midbrain DA neurons. Recently, Studer and colleagues were able to address these deficiencies and developed a protocol that allowed for differentiation of authentic midbrain DA neuronal cells, which are able to efficiently engraft in vivo (see, PCT Publn. No. WO2013/067362 to Studer et al., incorporated herein by reference). The methods and compositions provided herein expound upon the methods of Studer et al. to provide enhanced differentiation efficiency and high purity midbrain DA cell populations.

SUMMARY OF THE INVENTION

Embodiments of the present invention relate to improved methods for differentiation of midbrain DA neuronal cells from a population of pluripotent stems cells.

Thus, a first embodiment of the invention concerns a method for providing an enriched population of midbrain DA neurons comprising: differentiating cells of a population of pluripotent cells to provide a neural lineage cell population; further differentiating cells of the neural lineage cell population to generate a cell population, which includes midbrain neurons; and purifying cells from said cell population using a marker expressed from a pan-neural promoter, to provide an enriched population of midbrain DA neurons. In some aspects, methods of the embodiments further comprise use of a MEK inhibitor in midbrain DA cell differentiation, which enhances midbrain specification of a cell population. In still further aspects, a method of the embodiments does not comprise purification of cells using a DA-specific marker.

In certain aspects, purifying the cells using a marker according to the embodiments comprises selecting cells that express a screenable or selectable marker under the control of a pan-neural promoter. Thus, in some aspects, purifying the cells comprises selecting cells that express a selectable marker under the control of a pan-neural promoter, wherein the selectable marker is a drug resistance marker and the selecting is drug selection of cells that express a drug resistance marker. In certain aspects, the pan-neural promoter can be a TuJ-1, Map-2, Dcx, Synapsin, enolase 2, glial fibrillary acidic protein, or tubulin alpha-1A chain promoter. In further aspects, the screenable or selectable marker is integrated into the genome of the cells. For example, the marker may be integrated into the AAVS1 site of the genome. In alternative aspects, the screenable or selectable marker may be extra-chromosomal, such as carried on an episomal vector.

In still further aspects, purifying the cells using a marker in accordance with the embodiments comprises performing affinity purification of cells that comprise a surface marker expressed from pan-neural lineage. For example, a ligand or antibody to a surface marker can be used for purify cells. Various purification methodologies may be used according to the embodiments including, but not limited to, column purification, binding of cells a solid surface, such as bead (e.g., a magnetic bead) or use of fluorescence-activated cell sorting (FACS).

In certain aspects, a method of the embodiments comprises (a) obtaining a population of pluripotent cells; (b) culturing the population of cells in media comprising: a BMP inhibitor; a TGFβ inhibitor; an activator of Sonic hedgehog (SHH) signaling; and an activator of Wnt signaling; (c) transferring the cell population to a suspension culture in a media comprising a BMP inhibitor; an activator of SHH signaling; and an activator of Wnt signaling, thereby forming cell aggregates; (d) dissociating cell aggregates and seeding the dissociated cells into a matrix culture; (e) further differentiating the cell population in a maturation media comprising neuronal maturation factors to generate a cell population, which includes midbrain neurons; and (f) purifying the cells using a marker of pan-neural lineage, to provide an enriched population of midbrain DA neurons.

In further embodiments, a method is provided for providing an enriched population of midbrain DA neurons comprising obtaining a cell population, including midbrain neurons, and purifying cells from the cell population using a marker expressed from a pan-neural promoter, to provide an enriched population of midbrain DA neurons. In some aspects, the cells comprise an expression cassette comprising a marker gene under the control of the a pan-neural promoter (e.g., MAP2); and purifying cells comprises selecting cells that express the marker gene under the control of the pan-neural promoter, thereby providing an enriched population of midbrain DA neurons.

In a further embodiment there is provided a method for providing an enriched population of midbrain DA neurons comprising: obtaining a population of pluripotent cells; differentiating the cells into a into a neural lineage cell population in a medium comprising a MEK inhibitor (e.g., PD0325901) and, optionally, not containing exogenously added FGF8b; and further differentiating cells of the neural lineage cell population to provide an enriched population of midbrain DA neurons. Non-limiting examples of MEK inhibitors that could be used according to the embodiments include PD0325901, Trametinib (GSK1120212), Selumetinib (AZD6244), Pimasertib (AS-703026), MEK162, Cobimetinib, PD184352, BIX 02189, AZD8330 and PD98059. For example, the method can comprise culturing the cells in the presence of between about 0.1 and 10 µM (e.g., between about 0.1 and 5; 0.5 and 3 or 0.5 and 1.5 µM) of the MEK inhibitor, such as PD0325901. Thus, in certain aspects, differentiating the cells comprises culturing a population of pluripotent cells a media comprising a BMP inhibitor; a TGFβ inhibitor; an activator of Sonic hedgehog (SHH) signaling; an activator of Wnt signaling, a MEK inhibitor or a combination of the foregoing, wherein the media does not containing exogenously added FGF8b. In still further aspects, a method of the embodiments does not comprise purification of cells using a DA-specific marker. In some aspects, the pluripotent cells comprise a first expression cassette comprising a first marker gene under the control of pan-neural promoter as detailed above.

Thus, in some aspects, a method of the embodiments comprises (a) obtaining a population of pluripotent cells; (b) culturing the population of cells in media comprising: a BMP inhibitor; a TGFβ inhibitor; an activator of Sonic hedgehog (SHH) signaling; an activator of Wnt signaling (and optionally not containing exogenously added FGF8b); (c) transferring the cell population to a suspension culture in a media comprising a BMP inhibitor; an activator of SHH signaling; an activator of Wnt signaling; a MEK inhibitor; and, optionally, not containing exogenously added FGF8b, thereby forming cell aggregates; (d) dissociating cell aggregates and seeding the dissociated cells into a matrix culture; and (e) further differentiating the cell population to generate an enriched population of midbrain DA neurons.

In preferred aspects, pluripotent cells for use according to the embodiments are mammalian cells such as primate or human cells. For example, pluripotent cells may be from a patient having, at risk for or with symptoms of Parkinson's disease (PD). In especially preferred aspects, the cells are induced pluripotent stem (iPS) cells, such as iPS cells made from cells collected from a patient to be treated with DA neurons, or a bank of iPS cells.

In certain aspects, obtaining the population of midbrain DA neuronal cells comprises obtaining a population of pluripotent cells, said cells comprising a first expression cassette comprising a first marker gene under the control of the pan-neural promoter; and differentiating the cells into a population of cells including midbrain DA neurons. In some aspects, the cells may further comprise a second expression cassette. For example, the second expression cassette may comprise a marker gene, a reprogramming factor or a gene that promotes differentiation. In some aspects, a second expression cassette comprises a second marker gene, such as a marker gene under the control of the PGK promoter. The second expression cassette may be integrated into the genome of the cells or may be extra chromosomal (e.g., episomal). In a further aspect, obtaining a population of pluripotent cells may comprise selecting a population of pluripotent cells that express the second marker gene, such as a gene under the control of a PGK promoter. In further aspects, a second marker gene may be a drug selection marker and selecting a population of pluripotent cells may comprise culturing the cells in the presence of the drug.

In some aspects, a method of the embodiments may be performed over a period of about 20 to 200 days (e.g., between about 30-150, 30-120 or 30-100 day, or less than about 90 days). In a further aspect, at least 60%, 65%, 70%, 75%, 80%, 85%, 90%, 95%, 96%, 97%, 98% or 99% of the cells in the enriched population of midbrain DA neurons are positive for a marker of midbrain neurons or midbrain DA neurons. In further aspects, an enriched population of midbrain DA neurons produced by a method of the embodiments comprises at least $1 \times 10^2$, $1 \times 10^3$, $1 \times 10^4$, $1 \times 10^5$, or $1 \times 10^6$ midbrain DA neuron cells. In some aspects, neurons produced by the methods of the embodiments are sorted for at least a first marker of neurons, midbrain neurons or midbrain DA neurons.

In a further aspect, a method of the embodiments may comprise (a) obtaining a population of pluripotent cells (e.g., cells comprising an expression cassette comprising a marker gene under the control of the pan-neural promoter); (b) culturing the population of adherent cells in media comprising: a BMP inhibitor; a TGFβ inhibitor; an activator of Sonic hedgehog (SHH) signaling; an activator of Wnt signaling; and, optionally, a MEK inhibitor; (c) transferring the adherent cell population to a suspension culture in a medium (e.g., in a retinol- and retinoic acid-free medium) comprising a BMP inhibitor; an activator of SHH signaling; a myosin II inhibitor (e.g., blebbistatin); and an activator of Wnt signaling, thereby forming cell aggregates; (d) dissociating cell aggregates and seeding the dissociated cells on to a matrix culture; (e) maturing the cells in the matrix culture in a maturation medium comprising neuronal maturation factors; and, optionally, (f) purifying cells from the cell population using a marker of pan-neural lineage, thereby providing an enriched population of midbrain DA neurons.

Certain aspects of the embodiments concern differentiating pluripotent cells into a population of neuronal cells comprising midbrain DA neurons, wherein the differentiation is in a media comprising at least a first BMP signaling inhibitor. Non-limiting examples of inhibitors of BMP signaling include dorsomorphin, dominant-negative BMP, truncated BMP receptor, soluble BMP receptors, BMP receptor-Fc chimeras, noggin, LDN-193189, follistatin, chordin, gremlin, cerberus/DAN family proteins, ventropin, high dose activin, and amnionless. For example, in certain aspects, the BMP inhibitor of steps (b) or (c) may be LDN-193189 or noggin. For example, cells can be cultured in a media comprising about 1 to 1,000 nM LDN-193189 (e.g., between about 10 to 500, 50 to 500, 50 to 300 or about 200 nM LDN-193189). As used herein, a BMP signaling inhibitor may be referred to simply as a "BMP inhibitor."

Further aspects of the embodiments concern differentiating pluripotent cells into a population of neuronal cells comprising midbrain DA neurons, wherein the differentiation is in a media comprising at least a first TGFβ signaling inhibitor. Non-limiting examples of inhibitors of TGFβ signaling include A-83-01, GW6604, IN-1130, Ki26894, LY2157299, LY364947 (HTS-466284), LY550410, LY573636, LY580276, NPC-30345, SB-431542, SB-505124, SD-093, Sm16, SM305, SX-007, Antp-Sm2A, and LY2109761. For instance, the TGFβ inhibitor of step (b) may be SB431542. In some aspects, cells are cultured in a media comprising about 0.1 to 100 µM SB431542 (e.g., between about 1 to 100, 1 to 50, 5 to 20 or about 10 µM SB431542). As used herein, a TGFβ signaling inhibitor, including a TGFβ receptor inhibitor, may be referred to simply as a "TGFβ inhibitor."

Yet further aspects of the embodiments concern differentiating pluripotent cells into a population of neuronal cells comprising midbrain DA neurons, wherein the differentiation is in a media comprising at least a first activator of SHH signaling. For example, the activator of SHH signaling can be a recombinant SHH polypeptide (or a portion thereof) or a small molecule activator. In certain aspects, the activator of SHH of steps (b) or (c) may be Shh C25II, purmorphamine or a purmorphamine analogue (e.g., a Smoothened agonist, such as 3-chloro-N-[(1r,4r)-4-(methylamino)cyclohexyl]-N-[3-(pyridin-4-yl)benzyl]benzo[b]thiophene-2-carboxamide). Thus, in certain aspects, a culture media for use according to the embodiments comprises about 0.1 to 50 µM purmorphamine (e.g., between about 0.1 to 20, 0.5 to 10, 0.5 to 5 or about 2 µM purmorphamine). In further aspects, a culture media comprises about 1 to 1,000 ng/ml Shh C25II (e.g., between about 10 to 1,000, 10 to 500, 50 to 500 or about 100 ng/ml Shh C25II). In further aspects, the activator of SHH signaling of steps (b) or (c) may be Shh C25II and purmorphamine. For example, cells can be cultured in a media comprising about 0.1 to 50 µM purmorphamine and about 1 to 1,000 ng/ml Shh C25II.

Still further aspects of the embodiments concern differentiating pluripotent cells into a population of neuronal cells comprising midbrain DA neurons, wherein the differentiation is in a media comprising at least a first activator of Wnt signaling. For example, the activator of WNT signaling can be a glycogen synthase kinase 3 (GSK3) inhibitor. Non-limiting examples of inhibitors GSK3 inhibitors include NP031112, TWS119, SB216763, CHIR-98014, AZD2858, AZD1080, SB415286, LY2090314 and CHIR99021. In certain aspects, the activator of Wnt signaling of steps (b) or (c) may be CHIR99021. Thus, in some aspects, a culture media for use according to the embodiments comprises about 0.1 to 10 µM CHIR99021 (e.g., between about 0.1 to 5, 0.5 to 5, 0.5 to 3 or about 1.25 µM CHIR99021).

Thus, in certain aspects, step (b) may comprise culturing the cells for 1-6 days in an adherent culture system with a DMEM/F12 media comprising B27 supplement, 1 to 1,000 nM LDN-193189, 0.1 to 100 µM SB431542, 0.1 to 50 µM purmorphamine, 1 to 1,000 ng/ml Shh C25II, and 0.1 to 10 µM CHIR99021. In one aspect, the media may comprise B27 supplement, 200 nM LDN-193189, 10 µM SB431542, 2 µM purmorphamine, 100 ng/ml Shh C25II, and 1.25 µM CHIR99021. In some aspects, step (b) may comprise adding a MEK inhibitor to the media after 1-2 days of the step (b) culture. In certain aspects, the MEK inhibitor may be PD0325901 (e.g., about 1 µM PD0325901). In some aspects, step (b) may comprise culturing the cells in a media lacking exogenously added retinol or retinoic acid after 1-2 days of the step (b) culture. In some aspects, such a media does not comprise exogenously added FGF8.

In further aspects, step (c) may comprise dissociating the cells into single cells before transferring the cells to the suspension culture. For example, step (c) may comprise culturing the cells for 5-20 days in a suspension culture system with a media comprising DMEM/F12 comprising B27 supplement, 1 to 1,000 nM LDN-193189 and 0.1 to 10 µM CHIR99021, the media lacking exogenously added retinol or retinoic acid. In one aspect, the media may comprise B27 supplement, about 50-500 nM LDN-193189, and about 0.5-3 µM CHIR99021. In a further aspect, step (c) may comprise culturing the cells in a media comprising 1 to 100 µM blebbistatin (e.g., 1-50 µM or about 10 µM blebbistatin) for a portion of the 5-20 days of suspension culture. In still a further aspect, step (c) may comprise culturing the cells in a media comprising FGF (e.g., FGF8b) for a portion of the 5-20 days of suspension culture. In still further aspects, step (c) may comprise culturing the cells in a media comprising 0.1 to 10 µM purmorphamine and 10 to 1,000 ng/ml Shh C25II for a portion of the 5-20 days of suspension culture. In some aspects, purmorphamine may be used at a concentration of about 2 µM and Shh C25II may be used at a concentration of about 100 ng/ml. In further aspects, such a media does not comprise exogenously added FGF8.

In still further aspects, the dissociating of step (d) may comprise dissociating the cell aggregates into single cells. In some aspects, the matrix culture of step (d) may comprise extracellular matrix proteins, such as laminin, entactin, collagen or a mixture thereof (e.g., Matrigel®). In further aspects, the matrix culture of step (d) may comprise laminin, poly-lysine and/or poly-L-ornithine matrix components.

In yet further aspects, step (e) may comprise maturing the cells for 2-30 days in a maturation media comprising Neurobasal media comprising B27 supplement, L-glutamine, 1 to 50 ng/ml BDNF (e.g., 5-50, 10-30 or about 20 ng/ml BDNF), 1 to 50 ng/ml GDNF (e.g., 5-50, 10-30 or about 20 ng/ml GDNF), 0.1 to 10 ng/ml TGFβ (e.g., 0.1-5, 0.5-3 or about 1 ng/ml TGFβ, 1 to 1,000 µM ascorbic acid (e.g., 10-1,000, 50-500 or about 200 µM ascorbic acid), 10 to 2,000 µM bibutyryl cAMP (e.g., 10-1,000, 100-1,000 or about 500 µM bibutyryl cAMP), and 0.1 to 20 µM DAPT (e.g., 0.1-10, 1-10 or about 5 µM DAPT). In some aspects, the media lacks exogenously added retinol or retinoic acid. Thus, in one aspect, the Neurobasal media may comprise B27 supplement, L-glutamine, 20 ng/ml BDNF, 20 ng/ml GDNF, 1 ng/ml TGFβ, 200 µM ascorbic acid, 500 µM bibutyryl cAMP, and 5 µM DAPT. In some aspects, step (e) may comprise maturing the cells in a maturation media comprising 1 to 50 µM blebbistatin, such as about 2.5 µM blebbistatin, for a portion of the 2-30 days of culture.

Certain aspects of the embodiments concern cell aggregates formed during culture of pluripotent stem cells or progeny thereof. In some aspects, cell aggregates may be about, at least or at most 5, 10, 15, 20, 25, 30, 50, 100, 150, 200, 250, 300, 350, 400, 450, 500 µm in diameter. The diameter may be a mean, median or an average diameter. In another aspect, at least about 20%, 30%, 40%, 50%, 80%, 90%, 95%, or 99% (or any range derivable therein) of the aggregates may comprise at least or about 10, 15, 20, 25, 30, 35, 40, 45, 50, 80, 100, 150, 200, 250, 300, 400, 500, 1000 cells, or any range derivable therein. In certain aspects, a substantial portion (e.g., at least about 50%, 80%, 90%, 95%, 99% or any range derivable therein) of the aggregates are about 80 to 200 µm in diameter. The approximate uniformity of an optimal range of aggregate size may promote differentiation as differentiation is guided by spatial cues and interaction between various cell types, which can be manipulated by varying aggregate size.

Differentiation according to the embodiments comprises culturing pluripotent stem cells and/or progeny cells in an adherent or suspension culture. In a particular embodiment, during differentiation, the cell may be transferred to an adherent culture. For example, the adherent culture may have a non-cellular matrix component. In a preferable embodiment, the methods may be used for differentiation of pluripotent stem cells to produce neural cells in a suspension culture. Pluripotent stem cells or progeny cells thereof may be incubated in a suspension culture. In a further embodiment, pluripotent stem cell aggregates may be formed in a suspension culture. The suspension culture may have a volume of about, at least or at most 2 mL, 5 mL, 10 mL, 20 mL, 30 mL, 40 mL, 50 mL, 100 mL, 200 mL, 500 mL, 1 liters, 3 liters, 5 liters, 10 liters, 20 liters, 25 liters, 30, liters, 40 liters, 50 liters, or any range derivable therein, such as in a bioreactor. Some embodiments involve cells growing in a space whose volume is larger than a standard Petri dish or 96-well plate; consequently, some embodiments exclude the use of such containers.

To optimize the size and growth of the cell aggregates, the suspension culture may be moved at a speed of at least or about 5, 10, 15, 20, 30, 35, 40, 45, 50, 55, 60, 65, 70, 75, 80, 85, 90, 100 rpm, or any range of speed derivable therein. The movement may comprise stirring, shaking, rocking or rotating as non-limiting examples.

Differentiation according to the embodiments may start with or without dissociating the pluripotent stem cells. In some aspects, the differentiation may comprise dissociating the cells into an essentially single cell culture. The dissociation encompasses the use of any method known now or later developed that is capable of producing an essentially single cell culture. In an exemplary embodiment, the cells may be dissociated by a protease treatment or a mechanical treatment like pipetting. For example, the protease may be collagenase, trypsin-EDTA, dispase, or a combination thereof. Alternatively, a chelating agent may be used to dissociate the cells, such as sodium citrate, EGTA, EDTA or a combination thereof. An essentially single cell culture may be a cell culture wherein the cells desired to be grown are dissociated from one another, such that the majority of the cells are single cells, or at most two cells that remain associated (doublets). Preferably, greater than 50%, 60%, 70%, 80%, 90%, 95%, 96%, 97%, 98%, 99% or more of the cells desired to be cultured are singlets or doublets.

In some aspects, a marker gene may be a drug selection marker and step (f) may comprise selecting cells in maturation media comprising the drug. Alternatively, the first marker gene may be a screenable marker, and step (f) may comprise selecting cells (e.g., by FACS) based expression of the screenable marker.

In further embodiments an in vitro population of neuronal cells is provided wherein at least 60%, 65%, 70%, 75%, 80%, 85%, 90% or 95% of the cells are positive for forkhead box A2 (FoxA2; NCBI accession no. NP_068556.2, incorporated herein by reference) and/or LIM homeobox transcription factor 1 (Lmx1) (e.g., Lmx1-alpha (Lmx1a; NCBI accession no. NP_001167540.1, incorporated herein by reference) expression. In some aspects, at least about 75% or 80% of the cells in the population are positive for both Lmx1 and FoxA2 expression. For example, the cells can be positive for FoxA2 and/or Lmx1 as measure by in situ hybridization, immunofluorescence (IF) or flow cytometry. In further aspects, at least about 10%, 20%, 30%, 40%, 50%, 60%, 65%, 70%, 75%, 80%, 85% or 90% of the cells in the population are positive for tyrosine hydroxylase (TH; NCBI accession no. NP_954986.2, incorporated herein by reference) expression. In some aspects, a cell population of the embodiments comprises at least about 50,000, 100,000, 200,000, 300,000, 500,000, 1 million or 1.5 million cells (e.g., between about 500,000 and 2 million cells). In certain aspects, a cell population of the embodiments does not comprise any genetic modification (e.g., an integrated transgene). In further aspects, a cell population comprises a transgene, such as a screenable or selectable marker under the control of a pan-neural promoter as detailed herein. In still further aspects, cell populations of the embodiments are comprised in a tissue culture system or a pharmaceutically acceptable medium.

In still a further embodiment, an in vitro population of purified cells is provided, the population comprising midbrain DA neuron cells or pluripotent stem cells, said cells comprising a first expression cassette comprising a first marker gene under the control of a pan neural promoter. In some aspects, the cells of the embodiments may be mammalian cells, such as human cells. In certain aspects, the cells may be from a patient having, at risk of developing or with symptoms of Parkinson's disease. In some aspects, a population of purified cells may comprise midbrain DA neuron cells, wherein at least 80%, 85%, 90%, 95%, 96%, 97%, 98%, 99% or more of the cells are positive for a midbrain DA cell marker.

In yet a further embodiment a population of cells is provided comprising midbrain neurons, DA neurons, midbrain DA neurons or a mixture thereof. For example, a population of the embodiments can be composed of at least about 40%, 45%, 50%, 55%, 60%, 65%, 70%, 75%, 80%, 85% or 90% midbrain neurons and at least about 40%, 45%, 50%, 55%, 60%, 65%, 70%, 75%, 80%, 85% or 90% DA neurons (e.g., at least 50% midbrain neurons and at least 50% DA neurons). In some aspects, a population of cells is composed of at least 90%, 91%, 92%, 93%, 94%, 95%, 96%, 97%, 98%, 99% or more midbrain DA neurons (e.g., about 90%-98% or 95%-99% midbrain DA neurons). In still further aspects, a population of cells is provided comprising midbrain DA neurons, the population composed of at least 90%, 91%, 92%, 93%, 94%, 95%, 96%, 97%, 98%, 99% or more midbrain DA neurons (e.g., about 90%-98% or 95%-99% midbrain DA neurons). In some aspects, the population comprises midbrain DA neuron cells comprising a first expression cassette comprising a first marker gene under the control of a pan-neural promoter (e.g., the MAP2 promoter).

In yet a further embodiment a population of cells is provided in a stable freezing solution comprising viable midbrain neurons, viable DA neurons, viable midbrain DA neurons or a mixture thereof. In some aspects, a population of cells in a stable freezing solution is comprised of at least 60%, 65%, 70%, 75%, 80%, 85%, 90% or 95% cells that are positive for FoxA2 and/or Lmx1 expression. In further aspects, a population of the embodiments can be composed of at least about 40%, 45%, 50%, 55%, 60%, 65%, 70%, 75%, 80%, 85% or 90% viable midbrain neurons and at least about 40%, 45%, 50%, 55%, 60%, 65%, 70%, 75%, 80%, 85% or 90% viable DA neurons (e.g., at least 50% viable midbrain neurons and at least 50% viable DA neurons) after one freeze-thaw cycle. In some further aspects, a population of cells is provided comprising midbrain DA neurons in a stable freezing solution, the population composed of at least 40%, 50%, 60%, 70%, 80%, or 90% viable midbrain DA neurons after one freeze-thaw cycle. In some aspects, the population is composed of at least 40%, 50%, 60%, 70%, 80%, or 90% viable midbrain DA neurons after two, three or four freeze-thaw cycles. In still further aspects, the population is composed of 90%, 91%, 92%, 93%, 94%, 95%, 96%, 97%, 98%, 99% or more midbrain DA neurons (e.g., about 90%-98% or 95%-99% midbrain DA neurons). In some aspects, the population comprises midbrain DA neuron cells comprising a first expression cassette comprising a first marker gene under the control of a pan-neural promoter (e.g., the MAP2 promoter). A stable freezing solution of the embodiments in some aspects comprises one or more of a cell culture medium, a protease or protease cocktail, stabilizer (e.g., DMSO or glycerol), growth factor, buffers, or extracellular matrix components. In further aspects, there is provided a sealed vial comprising a population of midbrain DA neurons (e.g., a frozen population of cells) in a stable freezing solution wherein the population is composed of at least 90% viable midbrain DA neurons after one freeze-thaw cycle. In some aspects a vial of the embodiments comprises at least $1 \times 10^2$, $1 \times 10^3$, $1 \times 10^4$, $1 \times 10^5$, or $1 \times 10^6$ viable midbrain DA neuron cells.

Thus, in yet a further embodiment, there is provided a container labeled for use as a therapeutic modality for treatment of human disease, said container comprising a dosage of human dopaminergic neurons in the container, the human dopaminergic neurons being comprised of more than 70%, 75%, 80%, 85% or 90% neurons that are positive for FoxA2 and Lmx1 (e.g., Lmx1a) expression, the container supplied with a label describing the intended use of the neurons in treatment of human disease. In some aspects, a container of the embodiments comprises at least $1\times10^2$, $1\times10^3$, $1\times10^4$, $1\times10^5$, $1\times10^6$ or $1\times10^7$ (e.g., between about $1\times10^4$ and $1\times10^7$) viable neurons that are positive for FoxA2 and Lmx1 (e.g., Lmx1a) expression. In still further aspects, the cells are comprised in a stable freezing solution, such that at least 80%, 85% or 90% of the neurons are viable after one freeze-thaw cycle.

In still a further embodiment there is provided a method of producing a frozen population of midbrain DA neuron cells comprising (a) obtaining a culture of midbrain DA neuron cells; (b) separating the cells (e.g., into essentially single cells); (c) resuspending the cells in a stable freezing solution; and (d) freezing the population of DA neuron cells. In some aspects, separating the cells comprises mechanical separation and/or treatment of the cells with proteinase or a proteinase cocktail (e.g., Accutase®). For example, a proteinase treatment can be for 10, 20, 30, 40, 50 or more minutes. In further aspects, resuspending the cells in a stable freezing solution comprises resuspending cells in a solution comprising one or more of: a cell culture medium, a protease or protease cocktail, stabilizer (e.g., DMSO or glycerol), growth factor, buffers, or extracellular matrix components. In still further aspects, freezing the cells comprises freezing the cells in a controlled rate freezer.

In a further aspect a population of purified cells is provided comprising pluripotent stem cells comprising a marker gene under the control of a pan neural promoter (e.g., the MAP2 promoter). In one aspect, the pluripotent stem cells may be iPS cells.

In further aspects, a cell population of the embodiments comprises an expression cassette comprising a first marker gene under the control of a pan-neural promoter wherein marker gene may be a selectable marker. In some aspects, the first expression cassette may be integrated into the genome of the cells. In one aspect, the first expression cassette may be integrated into the AAVS1 site of the genome. In some aspects, a population of cells according to the embodiments may comprise at least $1\times10^2$, $1\times10^3$, $1\times10^4$, $1\times10^5$ or $1\times10^6$ cells.

In a further embodiment, a method of treatment is provided comprising (a) providing a population neurons (e.g., midbrain DA neurons) of the embodiments; and (b) transplanting cells from said population into the subject under conditions for allowing in vivo engraftment (i.e., for providing DA neuronal function). For example, in some aspects, the population of neurons comprises at least 60%, 65%, 70%, 75%, 80%, 85%, 90% or 95% cells that are positive for FoxA2 and/or Lmx1 (e.g., Lmx1a) expression (e.g., FoxA2 and Lmx1). In some aspects, the subject may show reduction of at least one of said neurological symptom. For example, the treatment may be a method for treating or reducing the symptoms of Parkinson's disease.

In still a further embodiment a method of screening a candidate drug is provided comprising (a) providing a population of neurons (e.g., midbrain DA neurons) according to the embodiments; (b) contacting the population of neurons with the candidate drug; and (c) determining the effect of the candidate drug on the cell population. For example, in some aspects, the population of neurons comprises at least 60%, 65%, 70%, 75%, 80%, 85%, 90% or 95% cells that are positive for FoxA2 and/or Lmx1, such as Lmx1a, expression (e.g., 60%, 65%, 70%, 75%, 80%, 85%, 90% or 95% cells that are positive for FoxA2 and Lmx1 expression). In certain aspects, determining the effect of the candidate drug may comprise assessing viability of cells in the population. Thus, in some aspects, a method may comprise screening a library of candidate drugs.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

Figure 1:
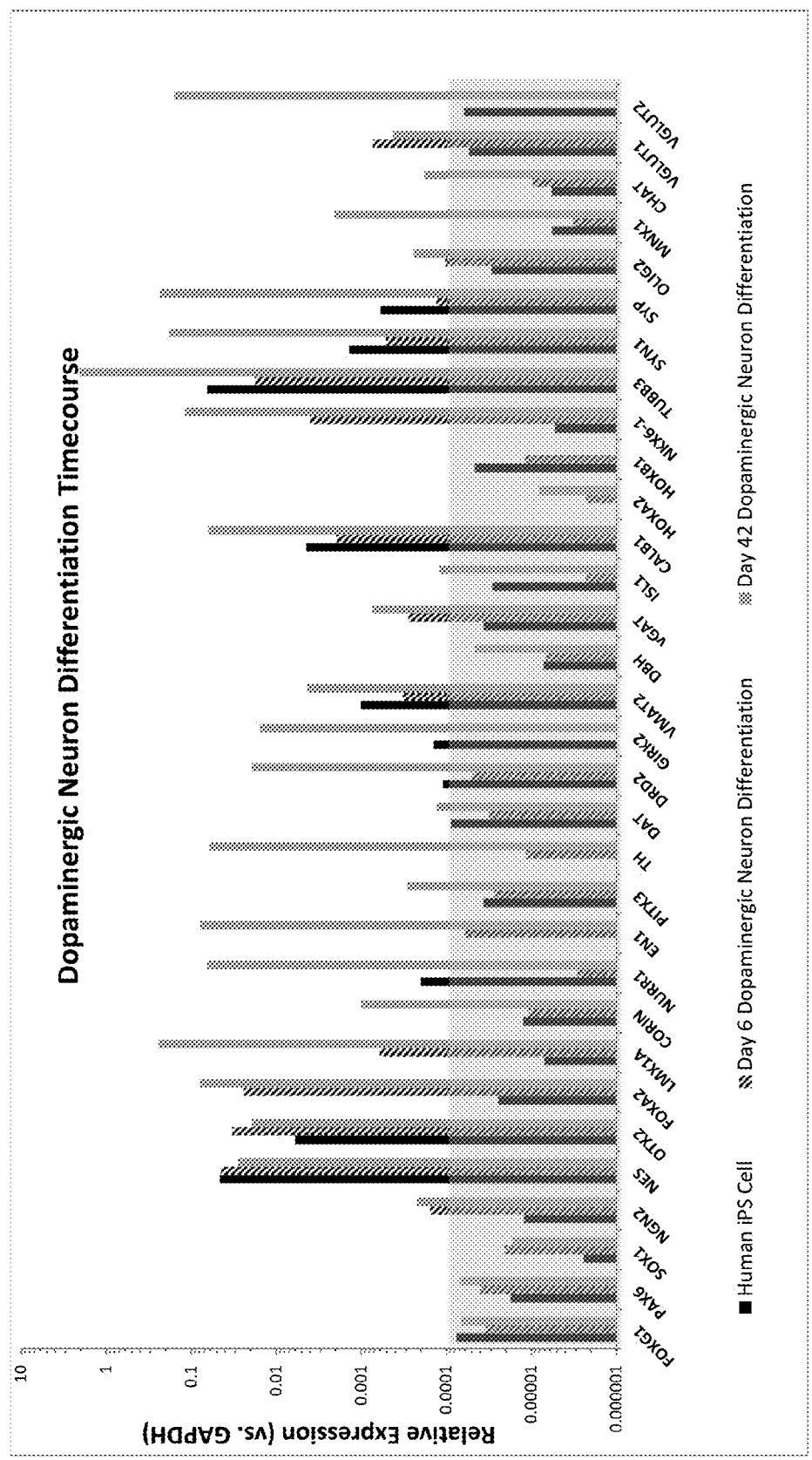
FIG. 1: Quantitative gene expression profile of cells before differentiation (human iPS cell), at Day 6 of the midbrain DA neuron differentiation process (Day 6 Dopaminergic neuron differentiation), and following the completion of the differentiation (Day 42). After RNA isolation, real-time quantitative polymerase chain reaction (PCR) was performed using TaqMan® Gene Expression Assays (Applied Biosystems), with results expressed as relative expression to GAPDH control. Values $<10^{-4}$ are considered background (shaded box). Neuralization was detected by day 6, as evidenced by the up-regulation of neuron subtype markers vGAT, Nkx6.1, vGLUT1, NGN2 and midbrain markers FoxA2, Lmx1a and OTX2. By day 42, additional genes expressed in midbrain DA neurons have been up-regulated (EN1, NURR1, TH, DRD2, GIRK2, VMAT2, DRD2, CALB1, TUBB3, SYN1, SYP, vGLUT2).
Figure 2:
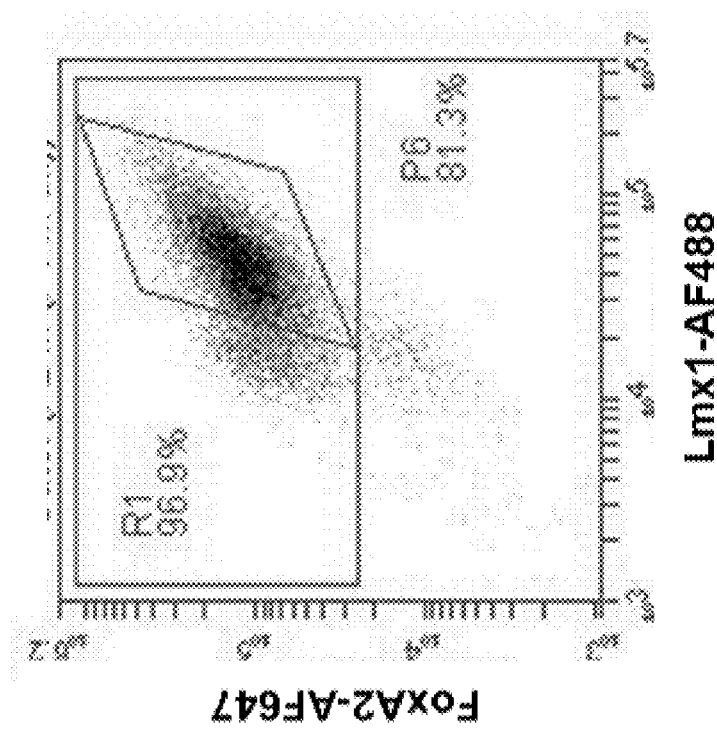
FIG. 2: Midbrain patterning of DA neuron progenitors. Co-expression of FoxA2 and Lmx1a is a specific marker for floor-plate derived midbrain DA neuron progenitors. By day 15 of the differentiation process, quantitative immunocytochemistry (ICC) using high content imaging demonstrated that >80% (81.7%) of the cells express both FoxA2 and Lmx1. Flow cytometry confirms this result, with only 16% of the cells being FoxA2$^+$/Lmx1$^-$ and 3% of the cells being FoxA2$^-$/Lmx1$^-$.

Lineage specific differentiated cell populations offer promise in cell replacement therapies for patients with diseases resulting in lose a defined cell population. Such cells are also valuable research tools for the study of disease and identification of new therapeutics. For example, production of midbrain DA neurons has been explored for the treatment and study of Parkinson's disease. Studer et al. recently developed a protocol that allowed for differentiation of authentic midbrain DA neuronal cells, which are able to efficiently engraft in vivo (PCT Publn. No. WO2013/067362, incorporated herein by reference). The methods and compositions detailed in the current application expand upon the Studer et al. protocol by providing methods having significantly enhanced differentiation efficiency and able to provide highly pure midbrain DA cell populations that have been shown to be engraftable in Sprague Dawley rats and non-human primates. Likewise, methods are provided for isolation of high purity midbrain DA cell compositions. For instance, it has been shown that use of cells that comprise a screenable or selectable marker under the control of a MAP2 promoter, allows for efficient selection (or screening) of midbrain DA neuronal cells. In particular, pluripotent cells can be engineered with the marker, differentiated into midbrain DA cells and then selected based upon the marker to achieve a purified population of midbrain DA cells. Likewise, it has been demonstrated that the use of a MEK inhibitor during midbrain DA cell differentiation, enhances midbrain specification of a cell population. Thus, by employing MEK inhibitor compositions in the differentiation protocol midbrain DA cells can be more efficiently and more quickly produced.

II. Definitions

"Pluripotency" refers to a stem cell that has the potential to differentiate into all cells constituting one or more tissues or organs, for example, any of the three germ layers:

endoderm (interior stomach lining, gastrointestinal tract, the lungs), mesoderm (muscle, bone, blood, urogenital), or ectoderm (epidermal tissues and nervous system).

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing or contacting with reprogramming factors.

"Embryonic stem (ES) cells" are pluripotent stem cells derived from early embryos.

"Adherent culture," refers to a culture in which cells, or aggregates of cells, are attached to a surface.

"Suspension culture," refers to a culture in which cells, or aggregates of cells, multiply while suspended in liquid medium.

"Essentially free" of an externally added component refers to a medium that does not have, or that have essentially none of, the specified component from a source other than the cells in the medium. "Essentially free" of externally added growth factors or signaling inhibitors, such as TGFβ, bFGF, TGFβ superfamily signaling inhibitors, etc., may mean a minimal amount or an undetectable amount of the externally added component. For example, a medium or environment essentially free of TGFβ or bFGF can contain less than 5, 4, 3, 2, 1, 0.9, 0.8, 0.7, 0.6, 0.5, 0.4, 0.3, 0.2, 0.1, 0.01, 0.001 ng/mL or any range derivable therein. For example, a medium or environment essentially free of signaling inhibitors can contain less than 0.2, 0.1, 0.09, 0.08, 0.07, 0.06, 0.05, 0.04, 0.03, 0.02, 0.01, 0.005, 0.001 μM, or any range derivable therein.

"Differentiation" is a process by which a less specialized cell forms progeny of at least a new cell type which is more specialized.

The term "aggregate promoting medium" means any medium that enhances the aggregate formation of cells without any restriction as to the mode of action.

The term "aggregates," i.e., embryoid bodies, refers to homogeneous or heterogeneous clusters of cells comprising differentiated cells, partly differentiated cells and/or pluripotent stem cells cultured in suspension.

"Neurons" or "neural cells" or "neural cell types" or "neural lineage" may include any neuron lineage cells, and can be taken to refer to cells at any stage of neuronal ontogeny without any restriction, unless otherwise specified. For example, neurons may include both neuron precursor cells, mature neurons and neural cell types such as astrocytes.

A "gene," "polynucleotide," "coding region," "sequence," "segment," or "fragment," which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "transgene," refers to a gene, nucleic acid, or polynucleotide which has been introduced into the cell or organism by artificial or natural means, such as an exogenous nucleic acid. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

III. Sources of Pluripotent Stem Cells

Pluripotent stem cells may be used in present methods for neural induction of pluripotent stem cells. Methods and compositions have been disclosed in the present invention to improve the neural differentiation efficiency by optimizing media component and/or selection of the desired midbrain DA neurons that are the product of the differentiation protocol.

The term "pluripotent stem cell" refers to a cell capable of giving rise to cells of all three germinal layers, that is, endoderm, mesoderm and ectoderm. Although in theory a pluripotent stem cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming somatic cells. In certain embodiments, the pluripotent stem cell is an embryonic stem cell derived by somatic cell nuclear transfer.

A. Embryonic Stem Cells

Embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, and then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, and then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thomson et al. In addition, subclones H9.1 and H9.2 of the H9 line have been developed. It is anticipated that virtually any ES or stem cell line known in the art and may be used with the present invention, such as, e.g., those described in Yu and Thomson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

B. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thomson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically requires the expression of or exposure to at least one member from the Sox family and at least one member from the Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10\times10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising an Oct family member and a Sox family member, such as Oct4 and Sox2 in combination with Klf or Nanog as describe above. The somatic cell in certain aspects of the present invention may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector, a chromosomally non-integrating RNA viral vector (see U.S. application Ser. No. 13/054,022, incorporated herein by reference) or an episomal vector, such as an EBV element-based system (see U.S. Application No. 61/058,858, incorporated herein by reference; Yu et al., 2009). In a further aspect, reprogramming proteins or RNA (such as mRNA or miRNA) could be introduced directly into somatic cells by protein or RNA transfection (see U.S. Application No. 61/172,079, incorporated herein by reference; Yakubov et al., 2010).

C. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, and then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

IV. Differentiation Conditions for Pluripotent Stem Cells

Depending on culture conditions, pluripotent stem cells can produce colonies of differentiated cells or undifferentiated cells. For example, pluripotent stem cells are cultured in a medium essentially free of grow factors like TGFβ and bFGF prior to differentiation, more particularly, prior to the induction of aggregate formation. Unless otherwise specified, differentiation is achieved by induction (e.g., aggregate formation), which may at least involve a change of culture conditions, but not by spontaneous changes.

Cultures of pluripotent stem cells are described as "undifferentiated" when a substantial proportion (e.g., at least about 50%, 80%, 90%, 95%, 99% or any range derivable therein) of stem cells and their derivatives in the population display morphological characteristics of undifferentiated cells, clearly distinguishing them from differentiated cells of embryo or adult origin. Undifferentiated ES or iPS cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

In certain aspects, starting cells for the present methods may comprise at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/mL, or any range derivable therein.

A. Medium for Differentiation

A differentiation medium according to certain aspects of the present invention can be prepared using a medium to be used for culturing animal cells as its basal medium. In some aspects the media comprises a BMP inhibitor; a TGFβ inhibitor; an activator of Sonic hedgehog (SHH) signaling; an activator of Wnt signaling and, optionally, and/or a MEK inhibitor. The medium may be a medium essentially free of TGFβ and bFGF. Any of the media used in differentiation may contain TGFβ and bFGF or may be a medium essentially free of TGFβ and bFGF. In certain aspects, the differentiation medium may obviate the need for externally added TGFβ superfamily signaling inhibitors and externally added bFGF inhibitors.

In certain aspects, a method of differentiation according to the embodiments involves passage of cell through a range of media conditions for example cell are cultured in adherent culture in a media comprising: a BMP inhibitor; a TGFβ inhibitor; an activator of Sonic hedgehog (SHH) signaling; and an activator of Wnt signaling;

in suspension in a media comprising a BMP inhibitor; an activator of SHH signaling; and an activator of Wnt signaling, to form cell aggregates;

in adherent culture in a Neurobasal media comprising B27 supplement, L-glutamine, BDNF, GDNF, TGFβ, ascorbic acid, bibutyryl cAMP, and DAPT, (and, optionally, lacking exogenously added retinol or retinoic acid) for maturation.

As the basal medium, any chemically defined medium, such as Eagle's Basal Medium (BME), BGJb, CMRL 1066, Glasgow MEM, Improved MEM Zinc Option, Iscove's modified Dulbecco's medium (IMDM), Medium 199, Eagle MEM, aMEM, DMEM, Ham, RPMI 1640, and Fischer's media, variations or combinations thereof can be used, wherein TGFβ and bFGF may or may not be included.

In further embodiments, the cell differentiation environment can also contain supplements such as B-27 supplement, an insulin, transferrin, and selenium (ITS) supplement, L-Glutamine, NEAA (non-essential amino acids), P/S (penicillin/streptomycin), N2 supplement (5 μg/mL insulin, 100 μg/mL transferrin, 20 nM progesterone, 30 nM selenium, 100 μM putrescine (Bottenstein, and Sato, 1979 PNAS USA 76, 514-517) and β-mercaptoethanol (β-ME). It is contemplated that additional factors may or may not be added, including, but not limited to fibronectin, laminin, heparin, heparin sulfate, retinoic acid.

Growth factors may or may not be added to a differentiation medium. In additional or in place of the factors outlined above, growth factors such as members of the epidermal growth factor family (EGFs), members of the fibroblast growth factor family (FGFs) including FGF2 and/or FGF8, members of the platelet derived growth factor family (PDGFs), transforming growth factor (TGF)/bone morphogenetic protein (BMP)/growth and differentiation factor (GDF) factor family antagonists may be employed at various steps in the process. Other factors that may or may not be added include molecules that can activate or inactivate signaling through Notch receptor family, including but not limited to proteins of the Delta-like and Jagged families as well as gamma secretase inhibitors and other inhibitors of Notch processing or cleavage such as DAPT. Other growth factors may include members of the insulin like growth factor family (IGF), the wingless related (WNT) factor family, and the hedgehog factor family.

Additional factors may be added in an aggregate formation and/or differentiation medium to promote neural stem/progenitor proliferation and survival as well as neuron survival and differentiation. These neurotrophic factors include but are not limited to nerve growth factor (NGF), brain derived neurotrophic factor (BDNF), neurotrophin-3 (NT-3), neurotrophin-4/5 (NT-4/5), interleukin-6 (IL-6), ciliary neurotrophic factor (CNTF), leukemia inhibitory factor (LIF), cardiotrophin, members of the transforming growth factor (TGF)/bone morphogenetic protein (BMP)/growth and differentiation factor (GDF) family, the glial derived neurotrophic factor (GDNF) family including but not limited to neurturin, neublastin/artemin, and persephin and factors related to and including hepatocyte growth factor. Neural cultures that are terminally differentiated to form postmitotic neurons may also contain a mitotic inhibitor or mixture of mitotic inhibitors including but not limited to 5-fluoro 2'-deoxyuridine, Mitomycin C and/or cytosine β-D-arabino-furanoside (Ara-C).

The medium can be a serum-containing or serum-free medium. The serum-free medium may refer to a medium with no unprocessed or unpurified serum and accordingly, can include media with purified blood-derived components or animal tissue-derived components (such as growth factors). From the aspect of preventing contamination with heterogeneous animal-derived components, serum can be derived from the same animal as that of the stem cell(s).

The medium may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR) and Chemically-defined Lipid concentrated (Gibco).

The medium can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example about 0.05 to 1.0 mM, and particularly about 0.1 to 0.5, or 0.01, 0.02, 0.03, 0.04, 0.05, 0.1, 0.2, 0.5, 0.8, 1, 1.5, 2, 2.5, 5, 7.5, 10 mM or any intermediate values, but the concentration is particularly not limited thereto as long as it is appropriate for culturing the stem cell(s).

The density of the pluripotent stem cell(s) to be differentiated is particularly not limited as far as it is a density at least or about 10, $10^1$, $10^2$, $10^3$, $10^4$, $10^5$, $10^6$, $10^7$, $10^8$ cells/cm$^2$ or at which the desired effects such as the improved neural induction can be achieved. It is, for example, about $1.0 \times 10^4$ to $1.0 \times 10^6$ cells/cm$^2$, more particularly about $2.0 \times 10^4$ to $6.5 \times 10^5$ cells/cm$^2$, and most particularly about $3.0 \times 10^4$ to $3.0 \times 10^5$ cells/cm$^2$.

In certain embodiments, pluripotent stem cells are cultured in a medium prior to aggregate formation to improve neural induction and floor plate patterning (e.g., prior to being dissociated into single cells or small aggregates to induce aggregate formation). In certain embodiments of the invention, the stem cells may be cultured in the absence of feeder cells, feeder cell extracts and/or serum.

B. Culture Conditions

A culture vessel used for culturing the cell(s) can include, but is particularly not limited to: flask, flask for tissue culture, spinner flask, dish, petri dish, dish for tissue culture, multi dish, micro plate, micro-well plate, multi plate, multi-well plate, micro slide, chamber slide, tube, tray, CellSTACK® Chambers, culture bag, and roller bottle, as long as it is capable of culturing the cells therein. The cells may be cultured in a volume of at least or about 0.2, 0.5, 1, 2, 5, 10, 20, 30, 40, 50, 100, 150, 200, 250, 300, 350, 400, 450, 500, 550, 600, 800, 1000, 1500 mL, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel surface can be prepared with cellular adhesive or not depending upon the purpose. The cellular adhesive culture vessel can be coated with any substrate for cell adhesion such as extracellular matrix (ECM) to improve the adhesiveness of the vessel surface to the cells. The substrate used for cell adhesion can be any material intended to attach stem cells or feeder cells (if used). Non-limiting substrates for cell adhesion include collagen, gelatin, poly-L-lysine, poly-D-lysine, poly-L-ornithine, laminin, vitronectin, and fibronectin and mixtures thereof, for example, protein mixtures from Engelbreth-Holm-Swarm mouse sarcoma cells (such as Matrigel™ or Geltrex) and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 7%, or any range derivable therein. The oxygen tension can be at least or about 1, 5, 8, 10, 20%, or any range derivable therein.

An adhesion culture may be used in certain aspects. In this case, the cells can be cultured in the presence of feeder cells. In the case where the feeder cells are used in the methods of the present invention, stromal cells such as fetal fibroblasts can be used as feeder cells (for example, refer to; Manipulating the Mouse Embryo A Laboratory Manual (1994); Gene Targeting, A Practical Approach (1993); Martin (1981); Evans et al. (1981); Jainchill et al., (1969); Nakano et al., (1996); Kodama et al. (1982); and International Publication Nos. 01/088100 and 2005/080554).

In other aspects, a suspension culture may be used. A suspension culture may include a suspension culture on carriers (Fernandes et al., 2007) or gel/biopolymer encapsulation (United States Patent Publication No. 2007/0116680). The suspension culture of the stem cells means that the stem cells are cultured under non-adherent conditions with respect to the culture vessel or feeder cells (if used) in a medium. The suspension culture of stem cells includes a dissociation culture of stem cells and an aggregate suspension culture of stem cells. The dissociation culture of stem cells means that suspended stem cells are cultured, and the dissociation culture of stem cells include those of single stem cells or those of small cell aggregates composed of a plurality of stem cells (for example, about 2 to 400 cells). When the aforementioned dissociation culture is continued, the cultured, dissociated cells form a larger aggregate of stem cells, and thereafter an aggregate suspension culture can be performed. The aggregate suspension culture includes an embryoid culture method (see Keller et al., 1995), and a SFEB (serum-free embryoid body) method (Watanabe et al., 2005); International Publication No. 2005/123902).

C. Culturing of Pluripotent Stem Cells

Methods for preparing and culturing pluripotent stem cells such as ES cells can be found in standard textbooks and reviews in cell biology, tissue culture, and embryology, including teratocarcinomas and embryonic stem cells: A practical approach (1987); Guide to Techniques in Mouse Development (1993); Embryonic Stem Cell Differentiation in vitro (1993); Properties and uses of Embryonic Stem Cells: Prospects for Application to Human Biology and Gene Therapy (1998), all incorporated herein by reference. Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

After somatic cells are introduced into or contacted with reprogramming factors, these cells may be cultured in a medium sufficient to maintain the pluripotency and the undifferentiated state. Culturing of induced pluripotent stem (iPS) cells can use various medium and techniques developed to culture primate pluripotent stem cells, more specially, embryonic stem cells, as described in U.S. Pat. Publication 2007/0238170 and U.S. Pat. Publication 2003/0211603, and U.S. Pat. Publication 2008/0171385, which are hereby incorporated by reference. It is appreciated that additional methods for the culture and maintenance of pluripotent stem cells, as would be known to one of skill, may be used with the present invention.

In certain embodiments, undefined conditions may be used; for example, pluripotent cells may be cultured on fibroblast feeder cells or a medium that has been exposed to fibroblast feeder cells in order to maintain the stem cells in an undifferentiated state. Alternately, pluripotent cells may be cultured and maintained in an essentially undifferentiated state using defined, feeder-independent culture system, such as a TeSR medium (Ludwig et al., 2006a; Ludwig et al., 2006b) or E8 medium (Chen et al., 2011; PCT/US2011/04679). Feeder-independent culture systems and media may be used to culture and maintain pluripotent cells. These approaches allow human pluripotent stem cells to remain in an essentially undifferentiated state without the need for mouse fibroblast "feeder layers." As described herein, various modifications may be made to these methods in order to reduce costs as desired.

Various matrix components may be used in culturing, maintaining, or differentiating human pluripotent stem cells. For example, collagen IV, fibronectin, laminin, and vitronectin in combination may be used to coat a culturing surface as a means of providing a solid support for pluripotent cell growth, as described in Ludwig et al. (2006a; 2006b), which are incorporated by reference in their entirety.

Matrigel™ may also be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

D. Single Cell Passaging

In some embodiments of pluripotent stem cell culturing, once a culture container is full, the colony is split into aggregated cells or even single cells by any method suitable for dissociation, which cells are then placed into new culture containers for passaging. Cell passaging or splitting is a technique that enables cells to survive and grow under cultured conditions for extended periods of time. Cells typically would be passaged when they are about 70%-100% confluent.

Single-cell dissociation of pluripotent stem cells followed by single cell passaging may be used in the present methods with several advantages, like facilitating cell expansion, cell sorting, and defined seeding for differentiation and enabling automatization of culture procedures and clonal expansion. For example, progeny cell clonally derivable from a single cell may be homogenous in genetic structure and/or synchronized in cell cycle, which may increase targeted differentiation. Exemplary methods for single cell passaging may be as described in U.S. Pat. Publn. 2008/0171385, which is incorporated herein by reference.

In certain embodiments, pluripotent stem cells may be dissociated into single individual cells, or a combination of single individual cells and small cell clusters comprising 2, 3, 4, 5, 6, 7, 8, 9, 10 cells or more. The dissociation may be achieved by mechanical force, or by a cell dissociation agent, such as NaCitrate, or an enzyme, for example, trypsin, trypsin-EDTA, TrypLE Select, or the like.

Based on the source of pluripotent stem cells and the need for expansion, the dissociated cells may be transferred individually or in small clusters to new culture containers in a splitting ratio such as at least or about 1:2, 1:4, 1:5, 1:6, 1:8, 1:10, 1:20, 1:40, 1:50, 1:100, 1:150, 1:200, or any range derivable therein. Suspension cell line split ratios may be done on volume of culture cell suspension. The passage interval may be at least or about every 1, 2, 3, 4, 5, 6, 7, 8, 9, 10, 11, 12, 13, 14, 15, 16, 17, 18, 19, 20 days or any range derivable therein. For example, the achievable split ratios for the different enzymatic passaging protocols may be 1:2 every 3-7 days, 1:3 every 4-7 days, and 1:5 to 1:10 approximately every 7 days, 1:50 to 1:100 every 7 days. When high split ratios are used, the passage interval may be extended to at least 12-14 days or any time period without cell loss due to excessive spontaneous differentiation or cell death.

In certain aspects, single cell passaging may be in the presence of a small molecule effective for increasing cloning efficiency and cell survival, such as a ROCK inhibitor or myosin II inhibitor as described above. Such a ROCK inhibitor or myosin II inhibitor, e.g., Y-27632, HA-1077, H-1152, or blebbistatin, may be used at an effective concentration, for example, at least or about 0.02, 0.05, 0.1, 0.2, 0.5, 1, 2, 3, 4, 5, 10, 15, 20, 25, 30, 35, 40, 45, 50 to about 100 μM, or any range derivable therein.

E. Differentiation of Stem Cells

Methods may be provided to improve neural differentiation (in particular midbrain DA differentiation efficiency) efficiency of pluripotent stem cells. Differentiation of pluripotent stem cells can be induced in a variety of manners, such as in attached colonies or by formation of cell aggregates, e.g., in low-attachment environment, wherein those aggregates are referred to as embryoid bodies (EBs). The molecular and cellular morphogenic signals and events within EBs mimic many aspects of the natural ontogeny of such cells in a developing embryo. Methods for directing cells into neuronal differentiation are provided for example in U.S. Publn. No. 2012/0276063, incorporated herein by reference. More detailed and specific protocols for DA neuron differentiation are provided in PCT Publication No. WO2013/067362, incorporated herein by reference.

Embryoid bodies (EBs) are aggregates of cells derived from pluripotent stem cells, such as ES cells or iPS cells, and have been studied for years with mouse embryonic stem cells. In order to recapitulate some of the cues inherent to in vivo differentiation, certain aspects of the invention may employ three-dimensional aggregates (i.e., embryoid bodies) as an intermediate step. Upon the start of cell aggregation, differentiation may be initiated and the cells may begin to a limited extent to recapitulate embryonic development. Though they cannot form trophectodermal tissue (which includes the placenta), cells of virtually every other type present in the organism can develop. The present invention may further promote neural differentiation following aggregate formation.

Cell aggregation may be imposed by hanging drop, plating upon non-tissue culture treated plates or spinner flasks; either method prevents cells from adhering to a surface to form the typical colony growth. ROCK inhibitors or myosin II inhibitors may be used before, during or after aggregate formation to culture pluripotent stem cells.

Pluripotent stem cells may be seeded into aggregate promotion medium using any method known in the art of cell culture. For example, pluripotent stem cells may be seeded as a single colony or clonal group into aggregate promotion medium, and pluripotent stem cells may also be seeded as essentially individual cells. In some embodiments, pluripotent stem cells are dissociated into essentially individual cells using mechanical or enzymatic methods known in the art. By way of non-limiting example, pluripotent stem cells may be exposed to a proteolytic enzyme which disrupts the connections between cells and the culturing surface and between the cells themselves. Enzymes which may be used to individualize pluripotent stem cells for aggregate formation and differentiation may include, but are not limited to, trypsin, in its various commercial formulations, such as TrypLE, or a mixture of enzymes such as Accutase®. In certain embodiments, pluripotent cells may be added or seeded as essentially individual (or dispersed) cells to a culturing medium for culture formation on a culture surface.

For example, dispersed pluripotent cells are seeded into a culturing medium at a density of from about $10^4$ cells/mL to about $10^{10}$ cells/mL. More particularly, pluripotent cells are seeded at a density of from about $10^5$ cells/mL to about $10^7$ cells/mL, or about $0.5 \times 10^6$ cells/mL to about $3 \times 10^6$ cells/mL. In these embodiments, a culturing surface may be comprised of essentially any material which is compatible with standard aseptic cell culture methods in the art, for example, a non-adherent surface. A culturing surface may additionally comprise a matrix component as described herein. In certain embodiments, a matrix component may be applied to a culturing surface before contacting the surface with cells and medium.

Substrates that may be used to induce differentiation such as collagen, fibronectin, vitronectin, laminin, matrigel, and the like. Differentiation can also be induced by leaving the cells in suspension in the presence of a proliferation-inducing growth factor, without reinitiating proliferation (i.e., without dissociating the neurospheres).

One illustrative method comprises culturing the cells on a fixed substrate in a culture medium. A proliferation-inducing growth factor can then be administered to the cells. The proliferation inducing growth factor can cause the cells to adhere to the substrate (e.g., polyornithine-treated plastic or glass), flatten, and begin to differentiate into different cell types.

V. Non-Static Culture

In certain aspects, non-static culture could be used for culturing and differentiation of pluripotent stem cells. The non-static culture can be any culture with cells kept at a controlled moving speed, by using, for example, shaking, rotating, or stirring platforms or culture vessels, particularly large-volume rotating bioreactors. The agitation may improve circulation of nutrients and cell waste products and also be used to control cell aggregation by providing a more uniform environment. For example, rotary speed may be set to at least or at most about 25, 30, 35, 40, 45, 50, 75, 100 rpm, or any range derivable therein. The incubation period in the non-static culture for pluripotent stem cells, cell aggregates, differentiated stem cells, or progeny cells derived therefrom, may be at least or about 4 hours, 8 hours, 16 hours, or 1, 2, 3, 4, 5, 6 days, or 1, 2, 3, 4, 5, 6, 7 weeks, or any range derivable therein.

VI. Genetic Alteration of Cells

Embodiments of the invention concern invention concern cells (e.g., pluripotent cells or DA neurons) that have been genetic engineered. A cell is said to be "genetically altered" or "transgenic" when a polynucleotide has been transferred into the cell by any suitable means of artificial manipulation, or where the cell is a progeny of the originally altered cell that has inherited the polynucleotide. In some aspects, cells of the embodiments comprise an expression cassette comprising a first marker gene under the control of the MAP2 promoter (see, e.g., NCBI reference sequence NC_000002.11, which comprises the promoter (incorporated herein by reference)).

A variety of mechanisms can be employed for genetic engineering of the cells. For example, in the case where integration is at an essentially random site(s) in the genome, a polynucleotide can be introduced in a retroviral vector (e.g., a lentiviral vector), an adeno-associated virus vector (without a functional Rep gene) or as part of a transposon system, such as a piggyBac vector. In other aspects, the polynucleotide is integrated into a selected genomic site, for example, the nucleic acid can be integrated at the AAVS1 integration site (e.g., by use of an adeno-associated virus vector in the presence of a functional Rep gene). Likewise, in certain aspects, integration at a selected genomic site can be by homologous recombination. The efficiency of standard HR in mammalian cells is only $10^{-6}$ to $10^{-9}$ of cells treated (Capecchi, 1990). The use of meganucleases, or homing endonucleases, such as I-SceI have been used to increase the efficiency of HR. Both natural meganucleases as well as engineered meganucleases with modified targeting specificities have been utilized to increase HR efficiency (Pingoud and Silva, 2007; Chevalier et al., 2002). Another path toward increasing the efficiency of HR has been to engineer chimeric endonucleases with programmable DNA specificity domains (Silva et al., 2011). Zinc-finger nucleases (ZFN) are one example of such a chimeric molecule in which Zinc-finger DNA binding domains are fused with the catalytic domain of a Type IIS restriction endonuclease such as FokI (as reviewed in Durai et al., 2005; PCT/US2004/030606). Another class of such specificity molecules includes Transcription Activator Like Effector (TALE) DNA binding domains fused to the catalytic domain of a Type IIS restriction endonuclease such as FokI (Miller et al., 2011: PCT/IB2010/000154). As used herein, integration at a selected genomic site can comprise insertion of the nucleic acid molecules (or a portion thereof) between two contiguous nucleotide positions in the genome or between two nucleotide positions that are not contiguous (e.g., resulting in a replacement of intervening genomic sequences). For example, integration of the nucleic acid at selected genomic sites can comprise replacement of a gene exon, intron, promoter, coding sequence or an entire gene.

In certain embodiments of the invention, cells containing a desired nucleic acid construct may be identified in vitro or in vivo by including a marker in the expression vector, such as a selectable or screenable marker. Such markers would confer an identifiable change to the cell permitting easy identification of cells containing the expression vector, or help enrich or identify differentiated neural cells by using a tissue-specific promoter. For example, neuron-specific promoters may be used, including but not limited to, TuJ-1, Map-2, Dcx, Synapsin, enolase 2, glial fibrillary acidic protein, or tubulin alpha-1A chain.

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Usually the inclusion of a drug selection marker aids in the cloning and identification of transformants, for example, genes that confer resistance to blasticidin, neomycin, puromycin, hygromycin, DHFR, GPT, zeocin and histidinol are useful selectable markers.

In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker may be used so long as it is capable of being expressed simultaneously with the nucleic acid encoding a gene product. Further examples of selectable and screenable markers are well known to one of skill in the art.

VII. Use of Dopaminergic Neurons

The DA neurons provided by methods and compositions of certain aspects of the invention can be used in a variety of applications. These include but not limited to transplantation or implantation of the DA neurons in vivo; screening cytotoxic compounds, carcinogens, mutagens growth/regulatory factors, pharmaceutical compounds, etc., in vitro; elucidating the mechanism of neurodegeneration; studying the mechanism by which drugs and/or growth factors operate; gene therapy; and the production of biologically active products, to name but a few.

A. Test Compound Screening

Midbrain DA neurons of this invention can be used to screen for factors (such as solvents, small molecule drugs, peptides, and polynucleotides) or environmental conditions (such as culture conditions or manipulation) that affect the characteristics of DA neurons provided herein.

In some applications, stem cells (differentiated or undifferentiated) are used to screen factors that promote maturation of cells along the neural lineage, or promote proliferation and maintenance of such cells in long-term culture. For example, candidate neural maturation factors or growth factors are tested by adding them to stem cells in different wells, and then determining any phenotypic change that results, according to desirable criteria for further culture and use of the cells.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015). In certain aspects of the embodiments, cell produced by methods detailed herein may be used as test cells for standard drug screening and toxicity assays (e.g., to identify, confirm, and test for specification of function or for testing delivery of therapeutic molecules to treat cell lineage specific disease), as have been previously performed on primary neurons in short-term culture. Assessment of the activity of candidate pharmaceutical compounds generally involves combining the neurons provided in certain aspects of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on neurons cells, or because a compound designed to have effects elsewhere may have unintended neural side effects. Two or more drugs can be tested in combination (by combining with the cells either simultaneously or sequentially), to detect possible drug-drug interaction effects.

In some applications, compounds are screened initially for potential neurotoxicity. Cytotoxicity can be determined in the first instance by the effect on cell viability, survival, morphology, and leakage of enzymes into the culture medium. More detailed analysis is conducted to determine whether compounds affect cell function (such as neurotransmission) without causing toxicity.

B. Treatment of Diseases of the Central Nervous System

1. Disease of the Central Nervous System

Neural progenitor cells or stem cells can be transplanted to regenerate neural cells in an individual having a disease of the central nervous system. Such diseases can include, but are not limited to, neurodegenerative diseases, such as parkinsonism.

As used herein, term "parkinsonism" refers to a group of diseases that are all linked to an insufficiency of dopamine in the basal ganglia which is a part of the brain that controls movement. Symptoms include tremor, bradykinesia (extreme slowness of movement), flexed posture, postural instability, and rigidity. A diagnosis of parkinsonism requires the presence of at least two of these symptoms, one of which must be tremor or bradykinesia. The most common form of parkinsonism is idiopathic, or classic, Parkinson's disease (PD), but for a significant minority of diagnoses, about 15 percent of the total, one of the Parkinson's plus syndromes (PPS) may be present. These syndromes also known as atypical parkinsonism, include corticobasal degeneration, Lewy body dementia, multiple systematrophy, and progressive supranuclear palsy. In general, Parkinson's disease involves the malfunction and death of vital nerve cells in the brain primarily in an area of the brain called the substantia nigra. Many of these vital nerve cells make dopamine. When these neurons die off, the amount of dopamine decreases, leaving a person unable to control movement normally. The intestines also have dopamine cells that degenerate in Parkinson's disease patients, and this may be an important causative factor in the gastrointestinal symptoms that are part of the disease. A group of symptoms that an individual experiences varies from person to person. Primary motor signs of Parkinson's disease include the following: tremor of the hands, arms, legs, jaw and face, bradykinesia or slowness of movement, rigidity or stiffness of the limbs and trunk and postural instability or impaired balance and coordination.

2. Methods for Administering Cells

Stem cells or differentiated cells can be administered to a subject either locally or systemically. Methods for administering DA neurons to a subject are known in the art. If the patient is receiving cells derived from his or her own cells, this is called an autologous transplant; such a transplant has little likelihood of rejection.

Exemplary methods of administering stem cells or differentiated cells to a subject, particularly a human subject, include injection or transplantation of the cells into target sites (e.g., striatum and/or substantia nigra) in the subject. The stem cells and/or DA neurons can be inserted into a delivery device which facilitates introduction, by injection or transplantation, of the cells into the subject. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The stem cells can be inserted into such a delivery device, e.g., a syringe, in different forms. For example, the cells can be suspended in a solution, or alternatively embedded in a support matrix when contained in such a delivery device.

Support matrices in which the stem cells can be incorporated or embedded include matrices that are recipient-compatible and that degrade into products that are not harmful to the recipient. The support matrices can be natural (e.g., collagen, etc.) and/or synthetic biodegradable matrices. Synthetic biodegradable matrices include synthetic polymers such as polyanhydrides, polyorthoesters, and polylactic acid.

As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is known in the art. The solution is preferably sterile and fluid to the extent that easy syringability exists.

Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating stem cells as described herein in a pharmaceutically acceptable carrier or diluent and, as required, other ingredients enumerated above, followed by filtered sterilization.

3. Dosage and Administration

In one aspect, the methods described herein provide a method for enhancing engraftment of progenitor cells or DA neurons in a subject. In one embodiment, the subject can be a mammal. In another embodiment, the mammal can be a human, although the invention is effective with respect to all mammals.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of each active ingredient required to be administered depend on the judgment of the practitioner and are particular to each individual. However, suitable dosage ranges depend on the route of administration. Suitable regimes for administration are also variable.

4. Efficacy

The efficacy of a given treatment to enhance DA neuron engraftment can be determined by the skilled artisan. However, a treatment is considered "effective treatment," as the term is used herein, if any one or all of the signs or symptoms of e.g., poor DA neuron engraftment are altered in a beneficial manner, other clinically accepted symptoms are improved, or even ameliorated, e.g., by at least 10% following treatment with a cell population as described herein. Efficacy can also be measured by a failure of an individual to worsen as assessed by hospitalization, need for medical interventions (i.e., progression of the disease is halted), or incidence of engraftment failure. Methods of measuring these indicators are known to those of skill in the art and/or are described herein. Treatment includes any treatment of a disease in an individual or an animal (some non-limiting examples include a human or a mammal) and includes: (1) inhibiting the disease, e.g., preventing engraftment failure; or (2) relieving the disease, e.g., causing regression of symptoms. An effective amount for the treatment of a disease means that amount which, when administered to a mammal in need thereof, is sufficient to result in effective treatment as that term is defined herein, for that disease. Efficacy of an agent can be determined by assessing physical indicators of, for example, DA neuron engraftment, such as, e.g., tremor, bradykinesia, flexed posture, balance and coordination, etc. Efficacy can be assessed in animal models of Parkinson's Disease, for example, by performing behavioral tests, such as step tests and cylinder tests.

C. Distribution for Commercial, Therapeutic, and Research Purposes

For purposes of manufacture, distribution, and use, the neural cells of this invention are typically supplied in the form of a cell culture or suspension in an isotonic excipient or culture medium, optionally frozen to facilitate transportation or storage.

This invention also includes different reagent systems, comprising a set or combination of cells that exist at any time during manufacture, distribution, or use. The cell sets comprise any combination of two or more cell populations described in this disclosure, exemplified but not limited to programming-derived cells (neural lineage cells, their precursors and subtypes), in combination with undifferentiated stem cells or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Midbrain DA Production from Pluripotent Cells

Cell Line Engineering:

A human induced pluripotent stem (iPS) cell line was engineered with a construct encoding a neomycin resistance gene driven by the human MAP2 promoter and a puromycin resistance gene driven by the PGK promoter. The construct was inserted into the AAVS1 site using Zinc Finger nuclease-mediated homologous recombination. Following puromycin selection, the clone MAP2 Neo #2 was selected and propagated on Matrigel using dispase splitting and mTeSR1 medium. The cell line was transitioned to EDTA splitting and Essential 8 medium prior to freezing the master cell bank.

DA Progenitor Induction and Expansion:

On Day (−2), the MAP2 Neo #2 iPS cells were split using TrypLE dissociation enzyme (7 min) and plated onto Matrigel at $3.3\times10^4$ cells/cm$^2$ in Essential 8 medium containing 2.5 μM blebbistatin (37° C., 5% $CO_2$). The cells were fed with Essential 8 medium on Day (−1) and Day 0.

On Day 1 of differentiation, neural induction (via dual-SMAD inhibition, with a BMP- and TGFβ-signaling inhibitors), floor plate specification (via Sonic Hedgehog signaling), and midbrain DA neuron specification (via WNT signaling) were simultaneously induced. Day 1 medium was composed of DMEM/F12 with B27 Supplement and containing a cocktail of small molecule inhibitors and activators ("Induction Cocktail"): 200 nM LDN-193189, 10 μM SB431542, 2 μM purmorphamine, 100 ng/mL Shh C25II and 1.25 μM CHIR 99021. On Day 2 the cells were fed with the same medium, with the addition of 1 μM PD0325901, a MEK inhibitor that induces faster and more efficient midbrain specification (DMEM/F12 with B27+ Induction Cocktail+1 μM PD0325901). On Day 3 and Day 4, the cells were fed with DMEM/F12 with B27 (−Vitamin A)+Induction Cocktail+1 μM PD0325901.

On Day 5, cells were dissociated using TrypLE (15 min) and transferred to a spinner flask suspension culture to form aggregates. Cells were cultured at $1\times10^6$ cells/mL in DMEM/F12 with B27 (−Vit.A)+200 nM LDN-193189, 2 μM purmorphamine, 100 ng/mL Shh C25II, 1.25 μM CHIR 99021 and 10 μM blebbistatin (37° C., 7% $CO_2$). On Day 6, aggregates were settled, 66% of the medium was removed, and the aggregates were fed with DMEM/F12 with B27 (−Vit.A)+200 nM LDN-193189, 2 μM purmorphamine, 100 ng/mL Shh C25II and 1.25 μM CHIR 99021. On Days 7-10, the aggregates were fed daily (75% medium replacement) with DMEM/F12 with B27 (−Vit.A)+200 nM LDN-193189 and 1.25 μM CHIR 99021. On Days 11-16, DA progenitor expansion was amplified with the addition of FGF8b and an increase in CHIR99021 concentration: aggregates were fed daily (75% medium replacement) with DMEM/F12 with B27 (−Vit.A)+200 nM LDN-193189, 3 μM CHIR 99021 and 100 ng/mL FGF8b.

DA Neuron Maturation, Drug Selection and Cryopreservation:

On Day 17, aggregates were dissociated to a single-cell suspension using TrypLE (15 min). Cells were plated onto Matrigel at $5.2\times10^5$ cells/cm$^2$ in the same medium used on Days 11-16, with the addition of 2.5 μM blebbistatin (37° C., 5% $CO_2$). On Day 18, the medium was replaced with "Maturation Medium": Neurobasal with B27 (−Vit.A) (Gibco®) and Glutamax+20 ng/mL BDNF, 20 ng/mL GDNF, 1 ng/mL TGFβ3, 200 μM ascorbic acid, 500 μM dibutyryl cAMP and 5 μM DAPT. Cells were fed every other day (Days 18, 20 and 22) with Maturation Medium.

On Day 24, cells were dissociated using Accutase (45 min) and were re-plated at $3.1\times10^5$ cells/cm$^2$ onto flasks pre-coated with poly-L-ornithine and laminin (PLO/laminin) in Maturation Medium containing 2.5 μM blebbistatin. Cells were fed with Maturation Medium on Day 25. On Day 27 and Day 29, cells were fed with Maturation Medium containing 100 μg/mL G418 to select against cells not expressing the neomycin resistance gene under the control of a pan-neuronal MAP2 promoter.

On Day 31, cells were dissociated using Accutase (45 min) and were re-plated at $3.1\times10^5$ cells/cm$^2$ onto PLO/laminin flasks in Maturation Medium containing 100 μg/mL G418 and 2.5 μM blebbistatin. On Day 32, Day 34 and Day 36, cells were fed with Maturation Medium. On Day 38, cells were dissociated using Accutase (45 min) and cryopreserved in CryoStor CS 10 medium at $1.25\times10^7$ cells/mL using a controlled rate freezer.

Analysis of DA Neurons:

Quantitative gene expression profiles of cells were determined before differentiation (human iPS cell), at Day 6 of the midbrain DA neuron differentiation process (Day 6 Dopaminergic neuron differentiation), and following the completion of the differentiation (Day 42). After RNA isolation, real-time quantitative PCR was performed using TaqMan® Gene Expression Assays (Applied Biosystems), with results expressed as relative expression to GAPDH control. The results of these studies are shown in FIG. 1 and show that neuralization was detected by day 6, as evidenced by the up-regulation of neuron subtype markers vGAT, Nkx6.1, vGLUT1, NGN2 and midbrain markers FoxA2, Lmx1a and OTX2. By day 42, additional genes expressed in midbrain DA neurons were up-regulated (EN1, NURR1, TH, DRD2, GIRK2, VMAT2, DRD2, CALB1, TUBB3, SYN1, SYP, vGLUT2).

Figure 3:
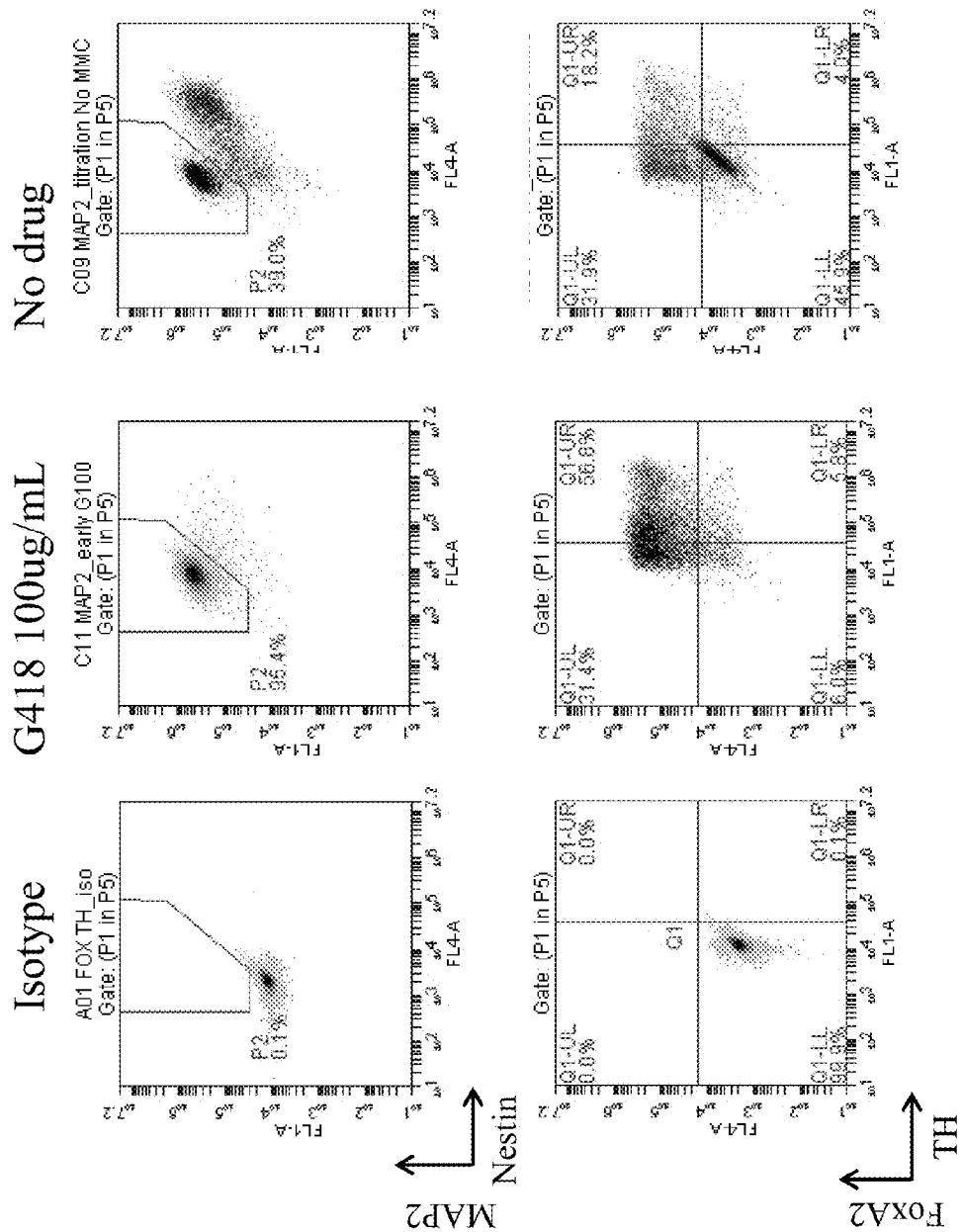
FIG. 3: Pan-neuron genetic selection for purification of midbrain DA neurons. Figure show flow cytometry results of iPS cells differentiated in neurons. iPS cell line MAP2 Nco #2 (01279.107.00402) was generated using zinc finger nuclease-mediated homologous recombination at the AAVS1 safe harbor site. The construct includes the Map2 promoter driving the expression of a neomycin resistance gene. The midbrain DA neuron differentiation protocol performed without drug selection resulted in a population of cells that is 39% neurons (Map2$^+$/Nestin$^-$) on day 38. The non-neuronal cells (Map2$^-$/Nestin$^+$) continued to proliferate and do not express FoxA2 or Tyrosine Hydroxylase (TH). Conversely, genetic drug selection with G418 resulted in a highly purified population of neurons (95% Map2$^+$/Nestin$^-$). Marker characterization demonstrated that the vast majority of these cells have the phenotype of midbrain DA neurons (see FIG. 4-FIG. 6).

Cells were further analyzed to determine co-expression of FoxA2 and Lmx1a (specific markers of floor-plate derived midbrain DA neuron progenitors). By day 15 of the differentiation process, quantitative ICC using high content imaging demonstrated that >80% (81.7%) of the cells express both FoxA2 and Lmx1. Flow cytometry analysis confirmed these results, with only 16% of the cells being FoxA2$^+$/Lmx1$^-$ and 3% of the cells being FoxA2$^-$/Lmx1$^-$ The effect of drug selection on gene expression in cell populations was also analyzed. FIG. 3 shows flow cytometry results of iPS cells differentiated in neurons. This iPS cell lines (MAP2 Neo #2 (01279.107.00402)) was generated using zinc finger nuclease-mediated homologous recombination at the AAVS1 safe harbor site, as detailed above. The midbrain DA neuron differentiation protocol performed without drug selection results in a population of cells that is 39% neurons (Map2$^+$/Nestin$^-$) on day 38. The non-neuronal cells (Map2$^-$/Nestin$^-$) continued to proliferate and did not express FoxA2 or Tyrosine Hydroxylase (TH). Conversely, genetic drug selection with G418 results in a highly purified population of neurons (95% Map2$^+$/Nestin$^-$). Further marker characterization (detailed below) demonstrated that the vast majority of these cells have the phenotype of midbrain DA neuron.

Figure 4:
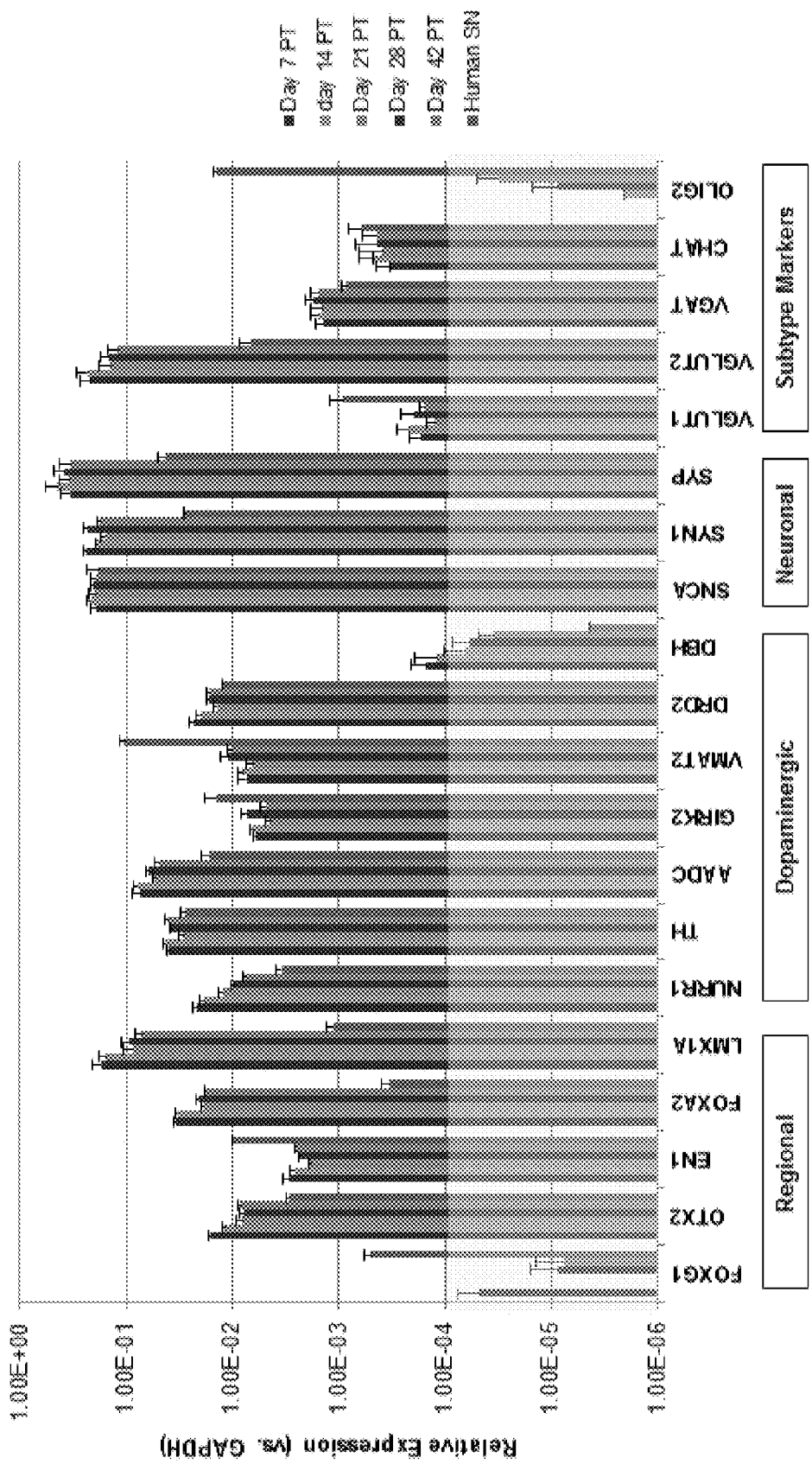
FIG. 4: Quantitative gene expression profile of post-thaw cells. Cells were cryopreserved on day 38 of the differentiation protocol, then thawed and plated on PLO/Laminin for the indicated times before RNA isolation. Real-time quantitative polymerase chain reaction (PCR) was performed using TaqMan® Gene Expression Assays (Applied Biosystems), with results expressed as relative expression to GAPDH control. Values<$10^{-4}$ are considered background (light shaded box). The cells expressed genes indicating a midbrain regionalization and markers for neurons, dopaminergic neurons, and floor plate-derived midbrain DA neurons. Markers for forebrain regionalization (FoxG1) or other neuronal subtypes (DBH, CHAT, OLIG2) were poorly expressed or negative. Most genes showed very similar expression levels across the tested post-thaw time course, up to 42 days post-thaw. The expression profile lines up well with that of RNA extracted from human midbrain substantia nigra (SN).

Cells were also analyzed to determine their gene expression profile at various time points post-thaw. Specifically, cells were cryopreserved on day 38 of the differentiation protocol, then thawed and plated on PLO/Laminin for the indicated times before RNA isolation. Real-time quantitative PCR was performed using TaqMan® Gene Expression Assays (Applied Biosystems), with results expressed as relative expression to GAPDH control. Results presented in FIG. 4 show that cells express genes indicating a midbrain regionalization and markers for neurons, dopaminergic neurons, and floor plate-derived midbrain DA neurons. Markers for forebrain regionalization (FoxG1) or other neuronal subtypes (DBH, CHAT, OLIG2) were poorly expressed or negative. Most genes showed very similar expression levels across the tested post-thaw time course, up to 42 days post-thaw. The expression profile lines up well with that of RNA extracted from human midbrain substantia nigra (SN).

Figure 5:
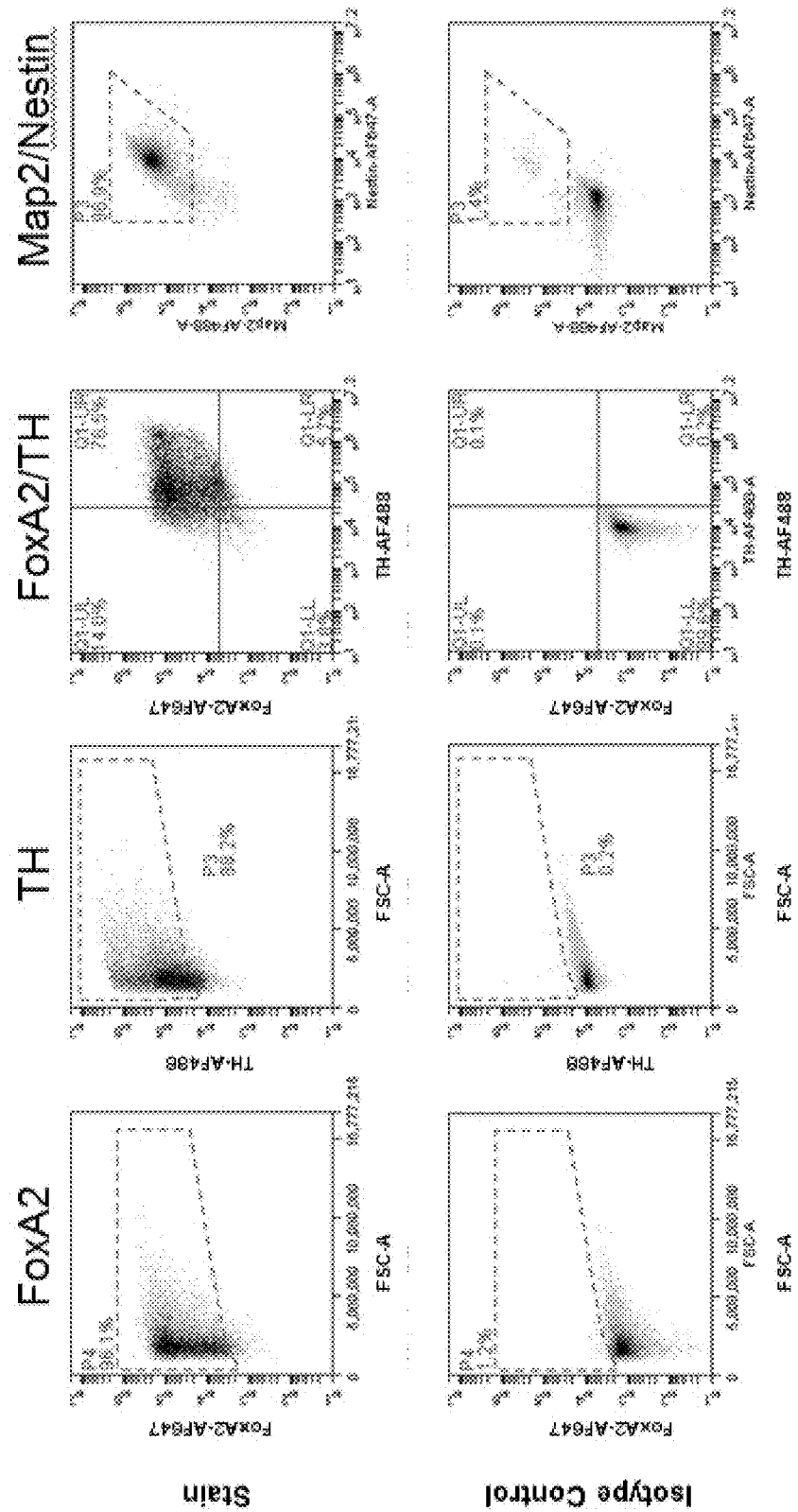
FIG. 5: Purity of mature midbrain DA neurons. FoxA2 expression was confirmed using flow cytometry, with 96% of the cells being FoxA2$^+$. The cells co-express the characteristic DA neuron marker tyrosine hydroxylase (TH) (88% compared to isotype control stain). In addition, 97% of the cells stain with the pan-neuron marker Map2.
Figure 6:
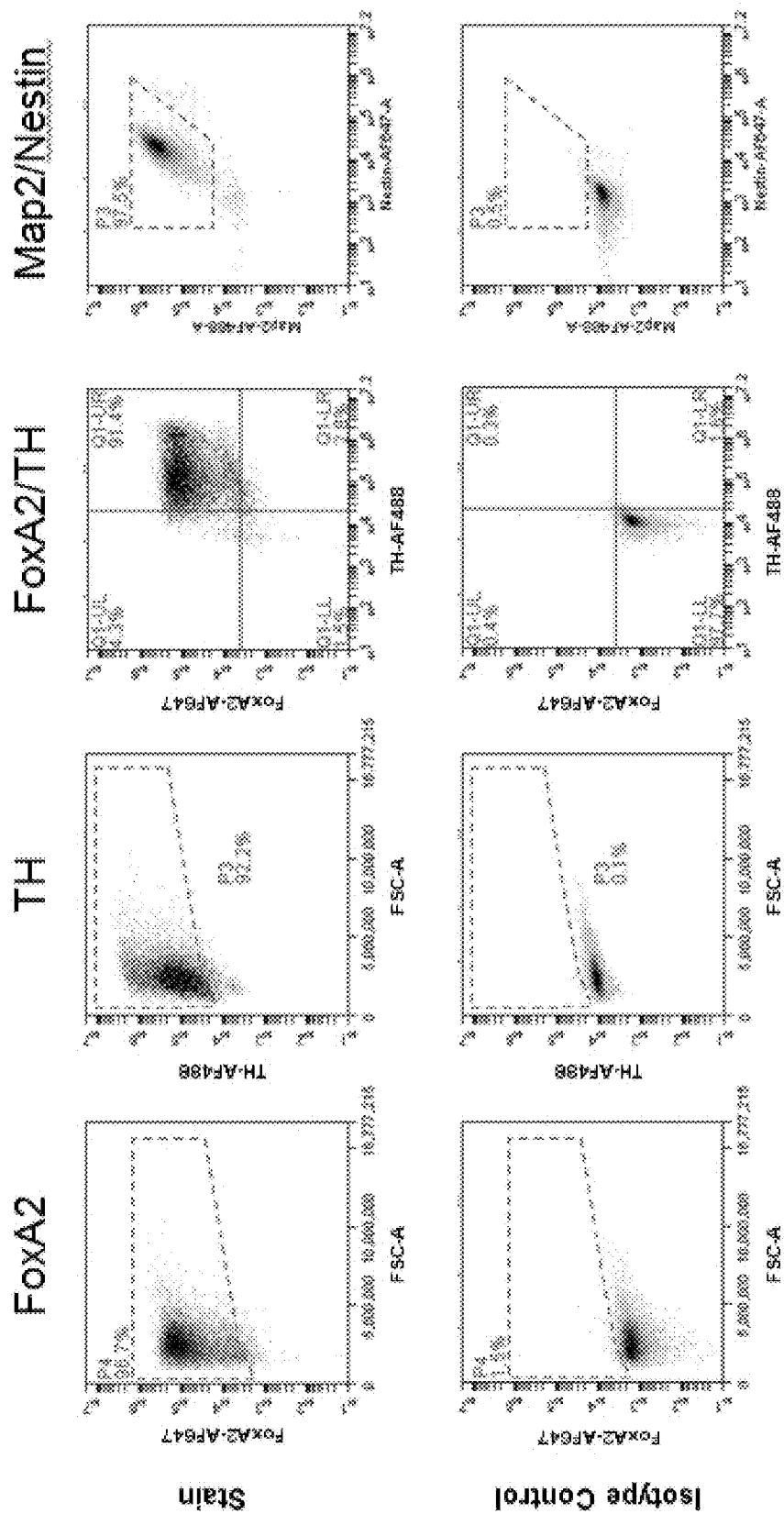
FIG. 6: Purity of mature midbrain DA neurons. Midbrain DA neuron phenotype were maintained even after extended post-thaw culturing. At day 14 post-thaw, TH expression levels have increased compared to day 3 post-thaw. Neuron purity is maintained (98%), with no outgrowth of Nestin$^+$ cells.

Cells were also examined (post-thaw) for co-expression of FoxA2 and Lmx1a. Specifically, cells were cryopreserved on day 38 of the differentiation protocol, then thawed and plated on PLO/Laminin for 7 days. Quantitative immunocytochemistry (ICC) using high content imaging demonstrates that 94% of the cells express FoxA2, 96% express Lmx1, and 91% of the cells express both FoxA2 and Lmx1. Thus, the midbrain phenotype is maintained in the vast majority of mature cells. FoxA2 expression was also confirmed using flow cytometry, with 96% of the cells being FoxA2⁻. The cells co-express the characteristic DA neuron marker tyrosine hydroxylase (TH) (88% compared to isotype control stain). In addition, 97% of the cells stained with the pan-neuron marker Map2 (see, FIG. 5). The midbrain DA neuron phenotype was maintained even after extended post-thaw culturing. At day 14 post-thaw, TH expression levels increased compared to day 3 post-thaw and neuron purity was maintained (98%), with no outgrowth of Nestin⁺ cells (see, FIG. 6).

In addition, DA neurons made with FGF8-containing medium according to the present Example have been found to be efficiently engrafted in Sprague Dawley rats and non-human primates.

Example 2—Midbrain DA Production from Pluripotent Cells, No FGF8/Early Cryopreservation Protocol Variation DA Progenitor Induction and Expansion:

On Day (−2), the MAP2 Neo #2 iPS cell line was split using TrypLE dissociation enzyme (7 min) and plated onto Matrigel at $3.3\times10^4$ cells/cm² in Essential 8 medium containing 2.5 µM blebbistatin (37° C., 5% $CO_2$). The cells were fed with Essential 8 medium on Day (−1) and Day 0.

On Day 1 of differentiation, neural induction (via dual-SMAD inhibition, with a BMP- and TGFβ-signaling inhibitors), floor plate specification (via Sonic Hedgehog signaling), and midbrain DA neuron specification (via WNT signaling) were simultaneously induced. Day 1 medium was composed of DMEM/F12 with B27 Supplement and containing a cocktail of small molecule inhibitors and activators ("Induction Cocktail"): 200 nM LDN-193189, 10 µM SB431542, 2 µM purmorphamine, 100 ng/mL Shh C25II and 1.25 µM CHIR 99021. On Day 2 the cells were fed with the same medium, with the addition of 1 µM PD0325901, a MEK inhibitor that induces faster and more efficient midbrain specification (DMEM/F12 with B27+Induction Cocktail+1 µM PD0325901). On Day 3 and Day 4, the cells were fed with DMEM/F12 with B27 (−Vitamin A)+Induction Cocktail+1 µM PD0325901.

On Day 5, cells were dissociated using TrypLE (15 min) and transferred to a spinner flask suspension culture to form aggregates. Cells were cultured at $1\times10^6$ cells/mL in DMEM/F12 with B27 (−Vit.A)+200 nM LDN-193189, 2 µM purmorphamine, 100 ng/mL Shh C25II, 1.25 µM CHIR 99021 and 10 µM blebbistatin (37° C., 7% $CO_2$). On Day 6, aggregates were settled, 66% of the medium was removed, and the aggregates were fed with DMEM/F12 with B27 (−Vit.A)+200 nM LDN-193189, 2 µM purmorphamine, 100 ng/mL Shh C25II and 1.25 µM CHIR 99021. On Days 7-9, the aggregates were fed daily (75% medium replacement) with DMEM/F12 with B27 (−Vit.A)+200 nM LDN-193189 and 1.25 µM CHIR 99021. On Days 10-12, the DA progenitor aggregates were fed daily (75% medium replacement) with DMEM/F12 with B27 (−Vit.A)+200 nM LDN-193189, and 3 µM CHIR 99021.

DA Neuron Maturation, Optional Drug Selection and Cryopreservation:

On Day 13, aggregates were dissociated to a single-cell suspension using TrypLE (15 min). Cells were plated onto Matrigel at $5.2\times10^5$ cells/cm² in the same medium used on Days 10-12, with the addition of 2.5 µM blebbistatin (37° C., 5% $CO_2$). On Day 14, the medium was replaced with "Maturation Medium": Neurobasal with B27 (−Vit.A) (Gibco®) and Glutamax+20 ng/mL BDNF, 20 ng/mL GDNF, 1 ng/mL TGFβ3, 200 µM ascorbic acid, 500 µM dibutyryl cAMP and 5 µM DAPT. Cells were fed every other day (Days 16 and 18) with Maturation Medium.

On Day 19, cells were dissociated using Accutase (45 min) and were re-plated at $3.1\times10^5$ cells/cm² onto flasks pre-coated with poly-L-ornithine and laminin (PLO/laminin) in Maturation Medium containing 2.5 µM blebbistatin. Cells were fed with Maturation Medium on Days 20, 22 and 24. To compare unselected cells to those that had undergone drug selection, in some experiments a side-arm condition of cells were fed on Day 22 and 24 with Maturation Medium containing 100 µg/mL G418 to select against cells not expressing the neomycin resistance gene under the control of a pan-neuronal MAP2 promoter.

On Day 26, cells were dissociated using Accutase (45 min) and cryopreserved in CryoStor CS 10 medium at $1.25\times10^7$ cells/mL using a controlled rate freezer.

Analysis of DA Neurons

Following cryopreservation cells were thawed and plated on PLO/Laminin. After 7 days, quantitative ICC using high content imaging was used to visualize cells having FoxA2 and Lmx1 expression. The results of these studies demonstrated that 83% (83.22%) of the cells express FoxA2, 84% (84.02%) express Lmx1, and 78% (77.97%) of the cells express both FoxA2 and Lmx1. Thus, the midbrain phenotype is maintained in the majority of mature cells.

Figure 7:
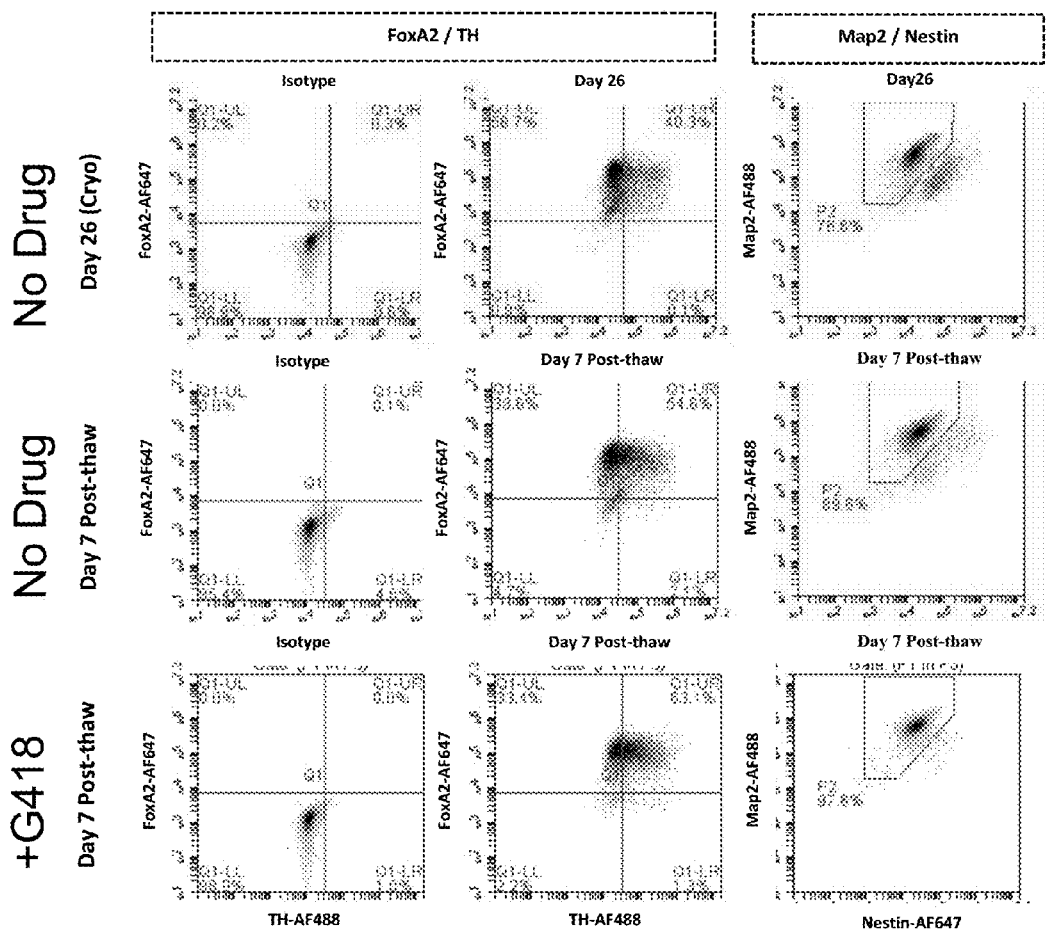
FIG. 7: Purity of mature midbrain DA neurons generated using protocol variation "No FGF8" in Example 2 was assessed by flow cytometry. This protocol variation was developed to obtain high purity midbrain DA neurons without the need for drug selection (i.e. without genetic modification of the iPS cells line) and cryopreservation soon after the cells stop dividing, changes that make the cells more amenable for implantation and clinical use. When the cells were cryopreserved on day 26 with no drug selection, they were 99% FoxA2$^+$, 40% TH$^+$, and 77% Map2$^+$. However, at this time point, Map2 and TH were still in the process of being up-regulated, and after 7 days of post-thaw culture, the final neuron (Map2) purity reached 90%, with 93% of the cells expressing FoxA2 and 55% expressing TH. For comparison, cells made using the same protocol but with drug selection (+G418), the final purity at 7 days post-thaw is 96% FoxA2$^+$, 63% TH$^+$, and 98% Map2$^+$.

In further studies the purity of mature midbrain DA neurons was assessed by flow cytometry of cells generated using a "no FGF8" protocol alone compared to cells obtained using a drug selection method. The results of these studies are shown in FIG. 7. When the cells are cryopreserved on day 26 with no drug selection, they are 99% FoxA2⁺, 40% TH⁺, and 77% Map2⁺. However, at this time point Map2 and TH were still in the process of being up-regulated, and after 7 days of post-thaw culture, the final neuron (Map2) purity had reached 90%, with 93% of the cells expressing FoxA2 and 55% expressing TH. For comparison, cells made using the same protocol but with drug selection (+G418), the final purity at 7 days post-thaw was 96% FoxA2⁺, 63% TH⁺, and 98% Map2⁺.

Figure 8:
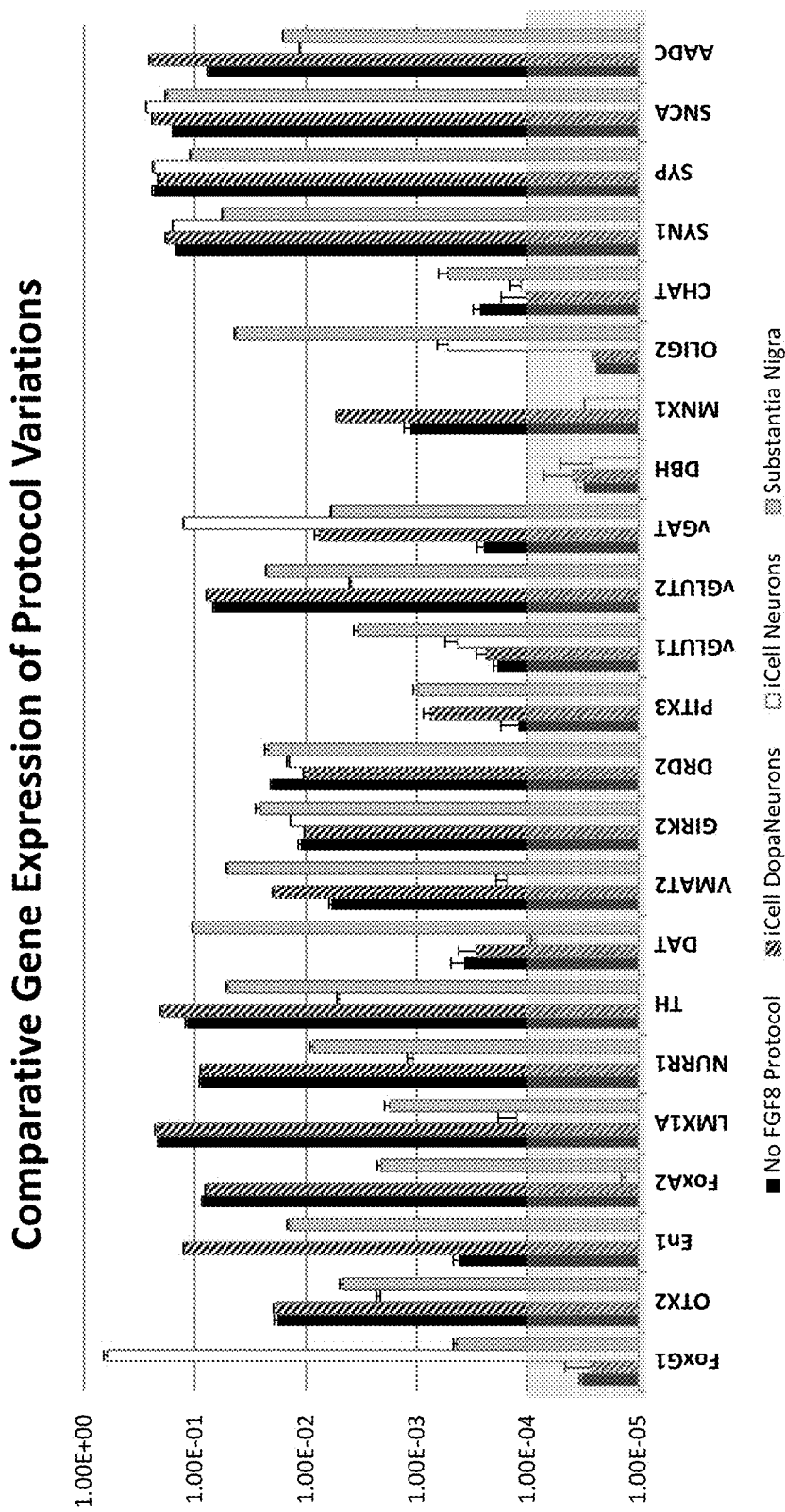
FIG. 8: Comparative gene expression of midbrain DA neuron protocol variations. RNA was isolated from cells differentiated as described in Example 1 (iCell DopaNeurons), or cells made with the "No FGF8" protocol described in Example 2, with G418 drug selection, and cryopreserved on day 33 (No FGF8 Protocol). For comparison, RNA was also isolated from stem cell-derived forebrain neurons (iCell Neurons) and human midbrain substantia nigra. Real-time quantitative polymerase chain reaction (PCR) was performed using TaqMan® Gene Expression Assays (Applied Biosystems), with results expressed as relative expression to GAPDH control. Values <$10^{-4}$ are considered background (shaded box). In most cases, the gene expression pattern of cells made using the No FGF8 protocol is very similar to that of the standard protocol with FGF8 (protocols of Example 1 vs. Example 2). One notable exception is the expression of Engrailed 1 (EN1), which is known to be upregulated by FGF8. Both expression profiles line up well with that of RNA extracted from human midbrain substantia nigra (SN). The expression profile of stem cell-derived forebrain neurons is markedly different, with decreased expression of midbrain DA neuron markers such as FoxA2, Lmx1, Nurr1, TH, vMAT2, vGLUT2 and AADC, and increased expression of the forebrain marker FoxG1.

Additional studies compared gene expression of midbrain DA neurons obtained with drug selection (see Example 1; iCell DopaNeurons) versus without drug selection (using a no FGF8 protocol of Example 2). For these experiments, RNA was isolated from differentiated cells and analyzed by TaqMan® Gene Expression Assays. For comparison, RNA was also isolated from stem cell-derived forebrain neurons (iCell Neurons) and human midbrain substantia nigra. The results are shown in FIG. 8 and demonstrate that, in most cases, the gene expression pattern of cells made using the no FGF8 protocol was very similar to that of the standard protocol with FGF8 (protocols of Example 1 vs. Example 2). One notable exception is the expression of Engrailed 1 (EN1), which is known to be upregulated by FGF8. Both expression profiles line up well with that of RNA extracted from human midbrain substantia nigra (SN). The expression profile of stem cell-derived forebrain neurons is markedly different, with decreased expression of midbrain DA neuron markers such as FoxA2, Lmx1, Nurr1, TH, vMAT2, and AADC, and increased expression of the forebrain marker FoxG1.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
U.S. Pat. No. 5,843,780
U.S. Pat. No. 6,200,806
U.S. Pat. No. 6,833,269
U.S. Pat. No. 7,029,913
U.S. Patent Appln. 61/058,858
U.S. Patent Appln. 61/172,079
U.S. Patent Appln. 61/184,546
U.S. Patent Publn. 2002/0168766
U.S. Patent Publn. 2003/0022367
U.S. Patent Publn. 2003/0211603
U.S. Patent Publn. 2003/0087919
U.S. Patent Publn. 2003/0125344
U.S. Patent Publn. 2004/0002507
U.S. Patent Publn. 2004/0002508
U.S. Patent Publn. 2004/0014755
U.S. Patent Publn. 2005/0192304
U.S. Patent Publn. 2005/0209261
U.S. Patent Publn. 2007/0116680
U.S. Patent Publn. 2007/0238170
U.S. Patent Publn. 2008/0171385
U.S. Patent Publn. 2011/0229441
U.S. Patent Publn. 2012/0276063
PCT/US2010/024487
PCT/US2011/046796
A practical approach, 1987
Andrews et al., In: *Teratocarcinomas and Embryonic Stem Cells*, Robertson (Ed.), IRL Press, 207-246, 1987.
Animal Cell Culture, 1987.
Bottenstein and Sato, *Proc. Natl. Acad. Sci. USA*, 76:514-517, 1979.
Byrne et al., *Nature*, 450(7169):497-502, 2007.
Chen et al., *Cell*, 133:1106-1117, 2008.
Chen et al., *Nature Methods* 8:424-429, 2011.
Current Protocols in Molecular Biology and Short Protocols in Molecular Biology, 1987 and 1995.
Doe et al., *J. Pharmacol. Exp. Ther.*, 32:89-98, 2007.
Embryonic Stem Cell Differentiation in vitro, 1993.
Evans et. al., *Nature*, 292:154, 1981.
Fernandes, et al., *J. Biotechnology*, 132(2):227-236, 2007.
Gene Targeting, A Practical Approach, IRL Press at Oxford University Press, 1993.
Gene Transfer Vectors for Mammalian Cells, 1987.
Greber et al., *Stem Cells*, 25:455-464, 2007.
Guide to Techniques in Mouse Development, 1993.
Harb et al., *PLoS One*, 20; 3(8):e3001, 2008.
International Patent Publication Nos. 2003/062227, 2003/059913, 2003/062225, 2002/076976 and 2004/039796,
International Publication No. 2005/123902
International Publication No. 2001/088100
International Publication No. 2005/080554
International Publication No. 2013/067362
Ishizaki, et al., *Mol. Pharmacol.*, 57:976-983, 2000.
Jainchill et al., *J. Virol.*, 4:549, 1969.
Keller et al., *Curr. Opin. Cell Biol.*, 7:862-869, 1995.
Kim et al, *Nature*, 418:50-56, 2002.
Klimanskaya et al., *Lancet.*, 365:P1636-1641, 2005.
Kodama et al., *J. Cell. Physiol.*, 112:89, 1982.
Krencik et al., *Nature Biotechnology* 29:528-534, 2011.
Krencik and Zhang, *Nature Protocols* 6(11):1710-1717, 2011.
Ludwig et al., *Nat. Biotechnol.*, 24(2):185-187, 2006b.
Ludwig et al., *Nat. Methods*, 3(8):637-46, 2006a.
Manipulating the Mouse Embryo A Laboratory Manual, Second Edition, Cold Spring Harbor Laboratory Press, 1994.
Martin, *Proc. Natl. Acad. Sci. USA*, 78:7634, 1981.
Nakajima et al., *Cancer Chemother. Pharmacol.*, 52:319-324, 2003.
Nakano et al., *Science*, 272, 722, 1996.
Ogawa et al., *J. Cell Sci.*, 120:55-65, 2007.
Perrier et al., *Proc. Natl. Acad. Sci. USA*, 101(34):12543-8, 2004.
Properties and uses of Embryonic Stem Cells: Prospects for Application to Human Biology and Gene Therapy, 1998.
Reubinoff et al., *Nat. Biotechnol.*, 18:399-404, 2000.
Sasaki et al., *Pharmacol. Ther.*, 93:225-232, 2002.
Schwartz et al., *Methods* 45(2): 142-158, 2008.
Smith, In: *Origins and Properties of Mouse Embryonic Stem Cells*, Annu Rev. Cell. Dev. Biol., 2000.
Sterneckert et al., *Stem Cells*, 28:1772-1781, 2010.
Suzuki et al., *Proc. Natl. Acad. Sci. USA*, 103:10294-10299, 2006.
Takahashi and Yamanaka, *Cell*, 126:663-676, 2006.
Takahashi et al., *Cell*, 126(4):663-76, 2007.
Takahashi et al., *Cell*, 131:861-872, 2007.
Thomson and Marshall, *Curr. Top. Dev. Biol.*, 38:133-165, 1998.
Thomson and Odorico, *J. Trends. Biotechnol.*, 18:53B57, 2000.
Thomson et al. *Proc. Natl. Acad. Scie. USA*, 92:7844-7848, 1995.
Thomson et al., *Science*, 282:1145, 1998.
Watabe and Miyazono, *Cell Res.*, 19:103-115, 2009.
Watanabe et al., *Nature Neurosci.*, 8:288-296, 2005.
Xu et al., *Cell Stem Cell*, 3:196-206, 2008.
Xu et al., *Nat. Biotechnol.*, 19:971-974, 2001.
Yakubov et al., *Biochemical and Biophysical Research Communications* 394: 189-193, 2010.
Ying et al., *Cell*, 115:281-292, 2003.
Yu and Thomson, *Genes Dev.* 22(15):1987-97, 2008.
Yu et al., *Science*, 318:1917-1920, 2007.
Yu et al., *Science*, 324(5928):797-801, 2009.

What is claimed is:
1. A method for providing an enriched population of midbrain dopaminergic (DA) neurons comprising:
differentiating cells of a population of human induced pluripotent cells to provide a neural lineage cell population;

further differentiating cells of the neural lineage cell population to generate a cell population which includes midbrain neurons; and purifying cells from said cell population using a transgenic screenable or selectable marker under the control of a pan-neural promoter expressed by cells of the cell population, to provide an enriched population of midbrain DA neurons, wherein the differentiation does not comprise culturing the cells in a medium containing exogenously added FGF8 and further wherein said differentiation steps are carried out in a chemically defined medium that is free of feeder cells and feeder cell extracts and at least 80% of cells in the enriched population are positive for both Lmx1 and FoxA2 expression.

2. The method of claim 1, wherein the enriched population of midbrain dopaminergic (DA) neurons comprise mammalian midbrain dopaminergic (DA) neuronal cells, at least about 85% the neuronal cells being positive for both LIM homeobox transcription factor 1 (Lmx1) and forkhead box A2 (FoxA2) expression.

3. The method of claim 2, wherein the neuronal cells comprise at least 500,000 cells.

4. The method of claim 3, wherein the neuronal cells comprise at least 1 million cells.

5. The method of claim 2, wherein at least about 80% of cells in the enriched population are positive for TH expression.

6. The method of claim 2, wherein the pan-neural promoter is a TuJ-1, Map-2, Dcx, Synapsin, enolase 2, glial fibrillary acidic protein, or tubulin alpha-1A chain promoter.

7. The method of claim 6, wherein the pan-neural promoter is the Map-2 promoter.

8. A method for providing an enriched population of midbrain dopaminergic (DA) neurons comprising:

obtaining a population of human induced pluripotent cells;

differentiating the cells into a neural lineage cell population in a medium comprising a MEK inhibitor and not containing exogenously added FGF8b; and further differentiating cells of the neural lineage cell population to provide an enriched population of midbrain DA neurons; and wherein said differentiation steps are carried out in chemically defined medium that is free of feeder cells and feeder cell extracts and at least 80% of cells in the enriched population are positive for both Lmx1 and FoxA2 expression.

* * * * *